(12) United States Patent
Hedrick et al.

(10) Patent No.: US 11,559,578 B2
(45) Date of Patent: Jan. 24, 2023

(54) BIODEGRADABLE CATIONIC POLYCARBONATES AS ADJUVANTS FOR VACCINES

(71) Applicant: International Business Machines Corporation, Armonk, NY (US)

(72) Inventors: James L. Hedrick, Pleasanton, CA (US); Yi Yan Yang, Singapore (SG); Ashlynn Lee, Singapore (SG); Chuan Yang, Singapore (SG)

(73) Assignee: International Business Machines Corporation, Armonk, NY (US)

( * ) Notice: Subject to any disclaimer, the term of this patent is extended or adjusted under 35 U.S.C. 154(b) by 224 days.

(21) Appl. No.: 16/916,860

(22) Filed: Jun. 30, 2020

(65) Prior Publication Data
US 2021/0401977 A1 Dec. 30, 2021

(51) Int. Cl.
| | |
|---|---|
| A61K 39/39 | (2006.01) |
| A61K 9/16 | (2006.01) |
| A61K 9/20 | (2006.01) |
| A61K 9/51 | (2006.01) |
| A61K 39/00 | (2006.01) |

(52) U.S. Cl.
CPC ............ *A61K 39/39* (2013.01); *A61K 9/1647* (2013.01); *A61K 9/204* (2013.01); *A61K 9/5153* (2013.01); *A61K 2039/54* (2013.01); *A61K 2039/6093* (2013.01)

(58) Field of Classification Search
CPC ............ A61K 39/39; A61K 2039/6093; A61K 2039/60993
See application file for complete search history.

(56) References Cited

U.S. PATENT DOCUMENTS

| | | | |
|---|---|---|---|
| 9,040,034 | B2 | 5/2015 | Hedrick et al. |
| 9,066,978 | B2 | 6/2015 | Ilyinskii et al. |
| 2005/0244505 | A1 | 11/2005 | Higbee et al. |
| 2011/0038888 | A1 | 2/2011 | Emtage |
| 2011/0293700 | A1 | 12/2011 | Bratzler et al. |

OTHER PUBLICATIONS

Wusiman et al, Cationic Polymer Modified PLAGA Nanoparticles Encapsulating Alhagi Honey Polysaccharides as a Vaccine Delivery System for Ovalbumin to Improve Immune Responses, International Journal of Nanomedicine; 14 3221-3234, (Year: 2019).*
Perez-Betancourt, Simple Nanoparticles from the Assembly of Cationic Polymer and Antigen as Immunoadjuvants, Vaccines , 8, 105. (Year: 2020).*
Azmi, Fazren et al., "Recent progress in adjuvant discovery for peptide-based subunit vaccines", Human Vaccines & Immunotherapeutics 10:3; Mar. 2014, 19 pages.

(Continued)

*Primary Examiner* — Carlos A Azpuru
(74) *Attorney, Agent, or Firm* — Stephen J. Walder, Jr.; Kristofer L. Haggerty

(57) ABSTRACT

A method for formation of a vaccine comprising combining a cationic polymer adjuvant with an antigen to form first immunoparticles through charge interactions and producing a treatment formulation for the vaccine comprising the first immunoparticles.

15 Claims, 26 Drawing Sheets

(56) References Cited

OTHER PUBLICATIONS

Lee, Ashlyn L. et al., "Subcutaneous vaccination using injectable biodegradable hydrogels for long-term immune response", Nanomedicine: Nanotechnology, Biology and Medicine, vol. 31, Oct. 2019, 10 pages.
Mužíkova, G. et al., "Macromolecular Systems for Vaccine Delivery", Physiol. Res. 65 (Suppl. 2): S203-S216, 2016, 14 pages.
Shakya, Akhilesh K. , "Polymers as immunological adjuvants: An update on recent developments", J. BioSci. Biotech. 2012, 1(3): 12 pages.
Varypataki, Eleni M. et al., "Cationic Liposomes Loaded with a Synthetic Long Peptide and Poly (I: C): a Defined Adjuvanted Vaccine for Induction of Antigen-Specific T Cell Cytotoxicity", The AAPS Journal, vol. 17, No. 1, Jan. 2015, 11 pages.

\* cited by examiner

| PN30-PLLA25/OVA NP | | | | | |
|---|---|---|---|---|---|
| MOLE RATIO OF PN30-PLLA25 TO OVA | 2:1 | 4:1 | 8:1 | 16:1 | 32:1 |
| SIZE (nm) | 104 ± 1 | 57 ± 1 | 56 ± 1 | 66 ± 1 | 97 ± 4 |
| PDI | 0.09 ± 0.03 | 0.23 ± 0.01 | 0.30 ± 0.02 | 0.48 ± 0.01 | 0.39 ± 0.05 |
| ZETA (mV) | 17.3 ± 0.1 | 19.5 ± 0.8 | 18.9 ± 1.0 | 31.1 ± 2.7 | 46.4 ± 1.4 |

FIG. 3A

| PN17-PLLA10/OVA NP | | | | | |
|---|---|---|---|---|---|
| MOLE RATIO OF PN17-PLLA10 TO OVA | 2:1 | 4:1 | 8:1 | 16:1 | 32:1 |
| SIZE (nm) | 155 ± 1 | 91 ± 1 | 49 ± 2 | 51 ± 1 | 58 ± 7 |
| PDI | 0.04 ± 0.01 | 0.16 ± 0.01 | 0.28 ± 0.01 | 0.37 ± 0.01 | 0.44 ± 0.06 |
| ZETA (mV) | 15.1 ± 0.1 | 17.3 ± 0.6 | 17.6 ± 1.0 | 16.3 ± 0.4 | 17.9 ± 1.5 |

FIG. 3B

| SAMPLES | POLY (I:C) ONLY | PN17-PLLA10/ I:C_0.1 NP | PN17-PLLA10/ I:C_0.5 NP | PN17-PLLA10/ I:C_2.5 NP |
|---|---|---|---|---|
| MASS RATIO OF PN17-PLLA10 TO POLY (I:C) | 0.5 mg/mL | 0.1 | 0.5 | 2.5 |
| SIZE (nm) | 84 ± 55 | 93 ± 1 | 91 ± 1 | 102 ± 1 |
| PDI | 0.71 ± 0.4 | 0.42 ± 0.01 | 0.18 ± 0.02 | 0.09 ± 0.03 |
| ZETA (mV) | -35.8 ± 5.8 | -39.9 ± 0.7 | -42.3 ± 1.6 | 27.6 ± 0.5 |

FIG. 3C

| MOLE RATIO OF PN17-PLLA10 TO OVA | 2:1 | 4:1 | 8:1 | 16:1 | 32:1 |
|---|---|---|---|---|---|
| | | | PN17-PLLA10/OVA/I:C | | |
| SIZE (nm) | 92 ± 1 | 126 ± 2 | 5565 ± 2 | 4805 ± 506 | 6367 ± 1722 |
| PDI | 0.17 ± 0.01 | 0.14 ± 0.01 | 0.24 ± 0.14 | 0.26 ± 0.02 | 0.50 ± 0.37 |
| ZETA (mV) | -41.5 ± 0.4 | -38.5 ± 1.1 | -8.8 ± 0.1 | 8.0 ± 0.7 | 19.9 ± 0.4 |

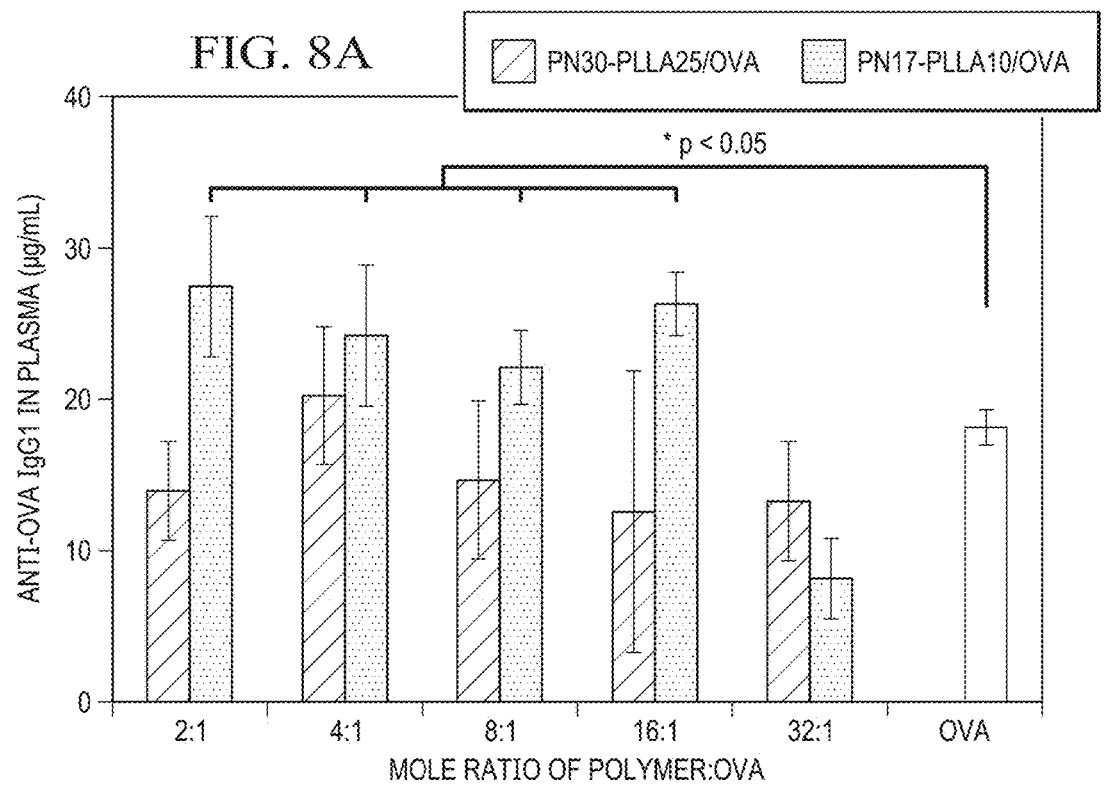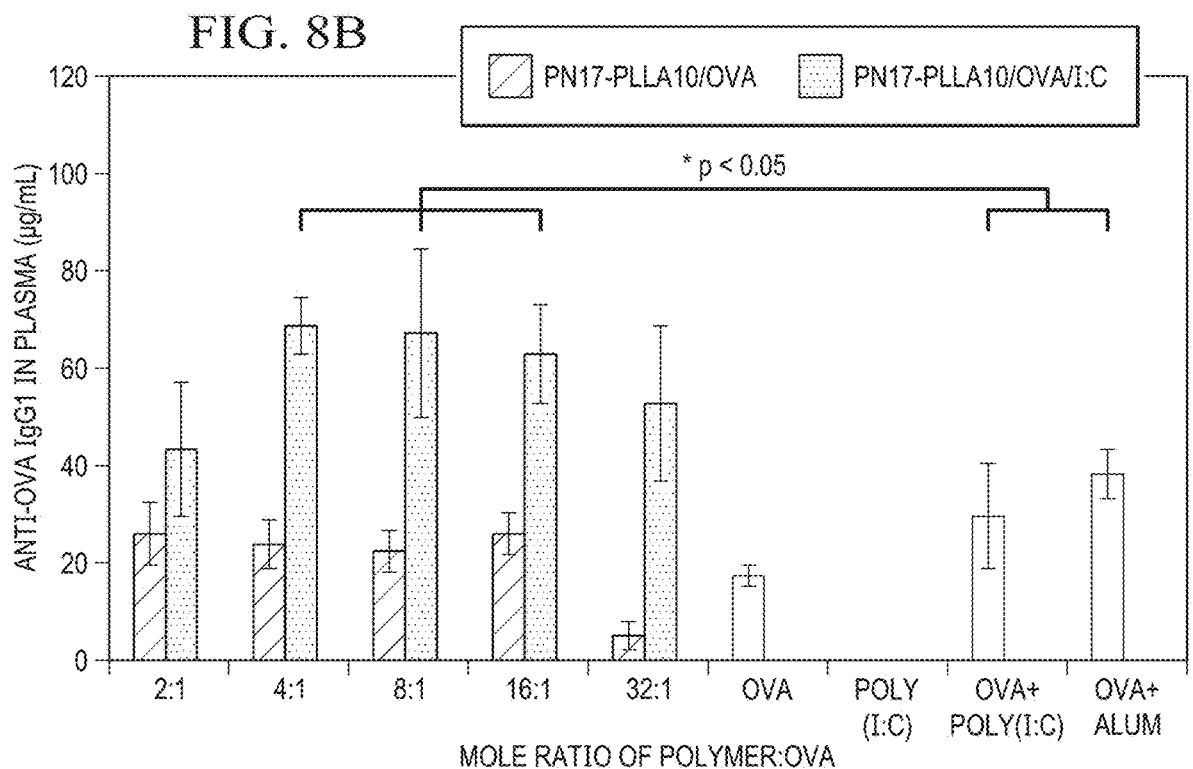

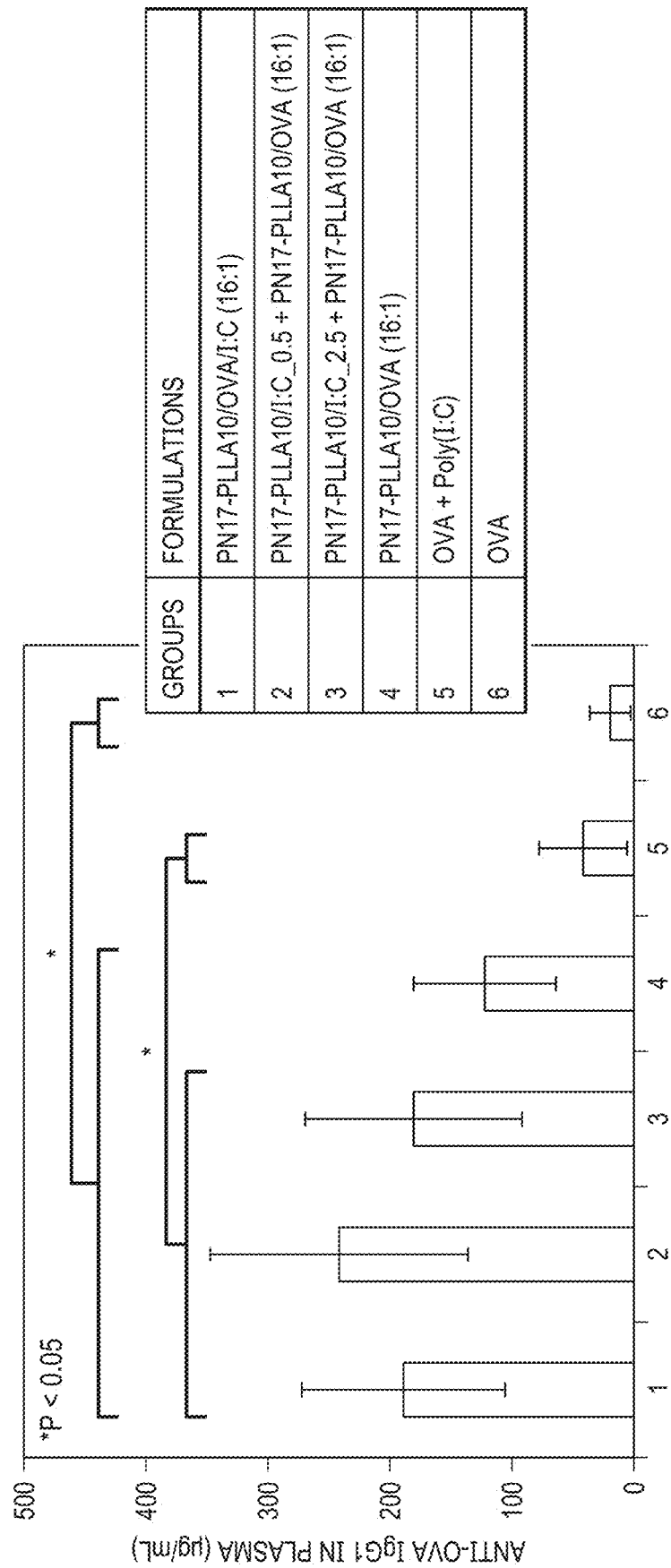

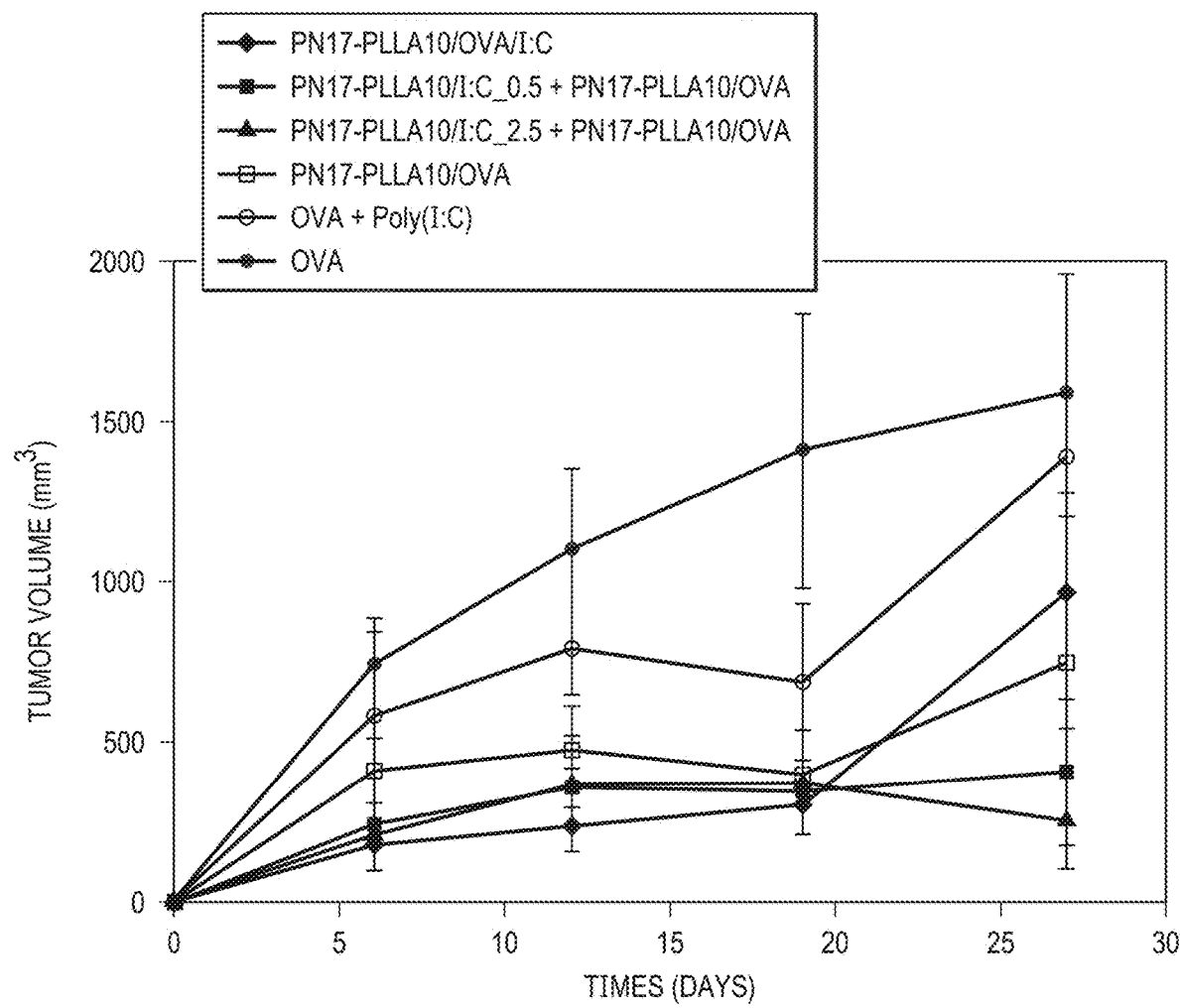

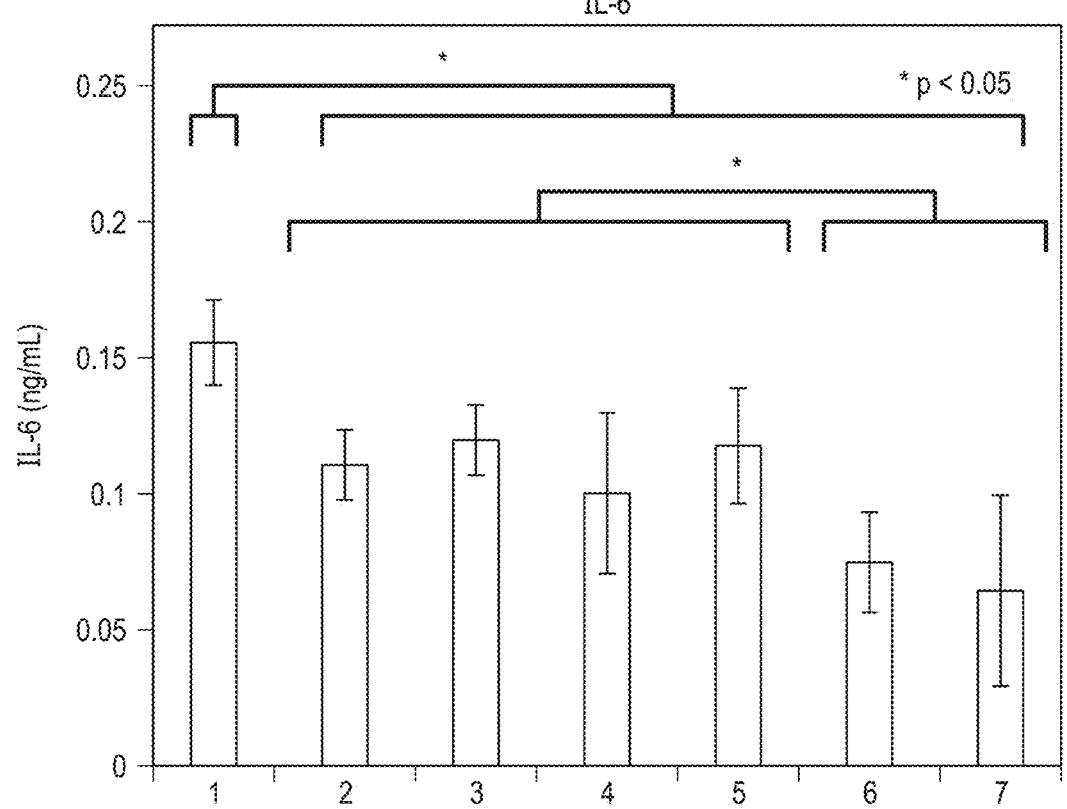

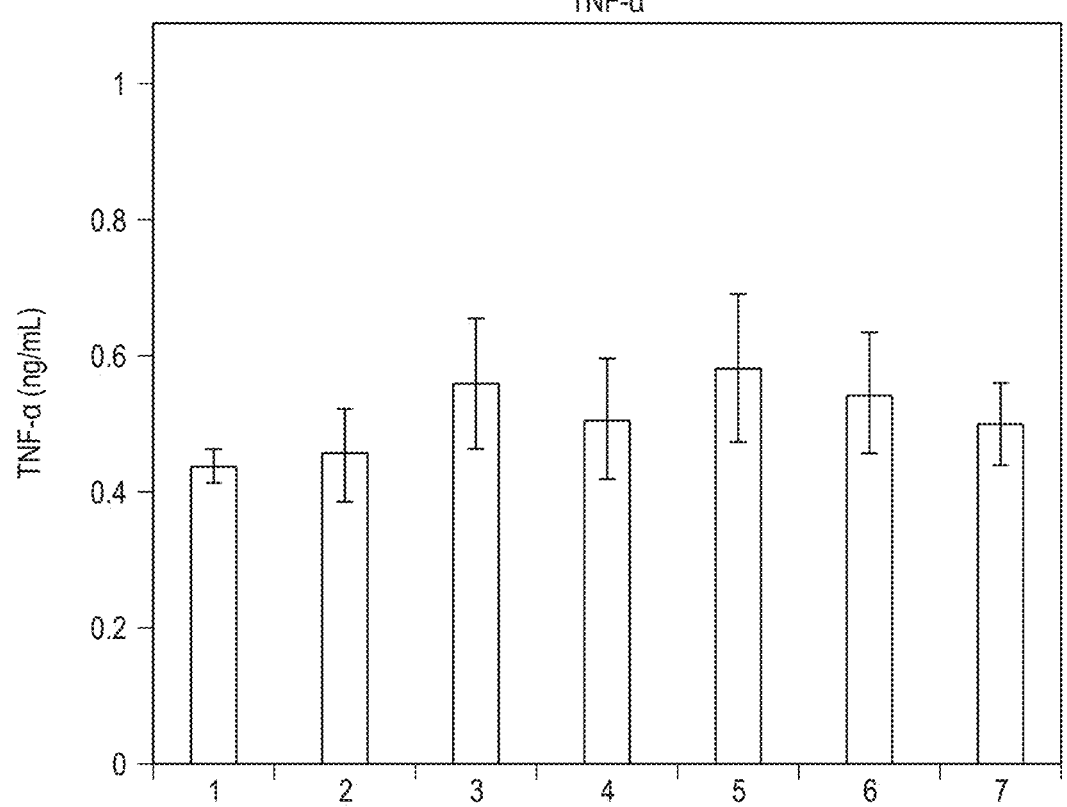

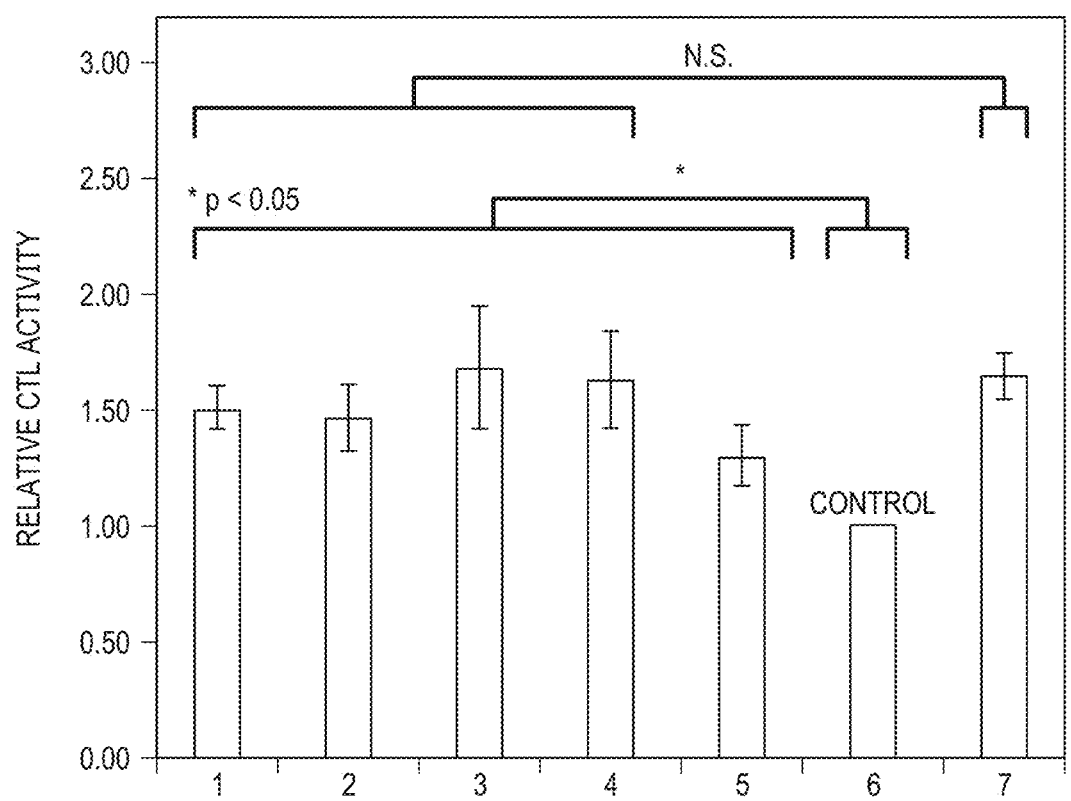

| SAMPLE | SIZE (nm) | PDI | ZP (mV) |
|---|---|---|---|
| PEt_Gua20/OVA (1:1) | 167 ± 4 | 0.04 ± 0.02 | 11.5 ± 0.3 |
| PEt_Gua20/OVA (1.9:1) | 83 ± 1 | 0.18 ± 0.02 | 27.6 ± 1.4 |
| PBut_Gua20/OVA (1:1) | 159 ± 10 | 0.11v± 0.04 | 12.1 ± 1.0 |
| PEt_Gua20/IC_2.5 | 79 ± 1 | 0.16 ± 0.01 | 47.1 ± 1.5 |
| PBut_Gua20/IC_2.5 | 74 ± 1 | 0.20 ± 0.06 | 49.8 ± 0.6 |

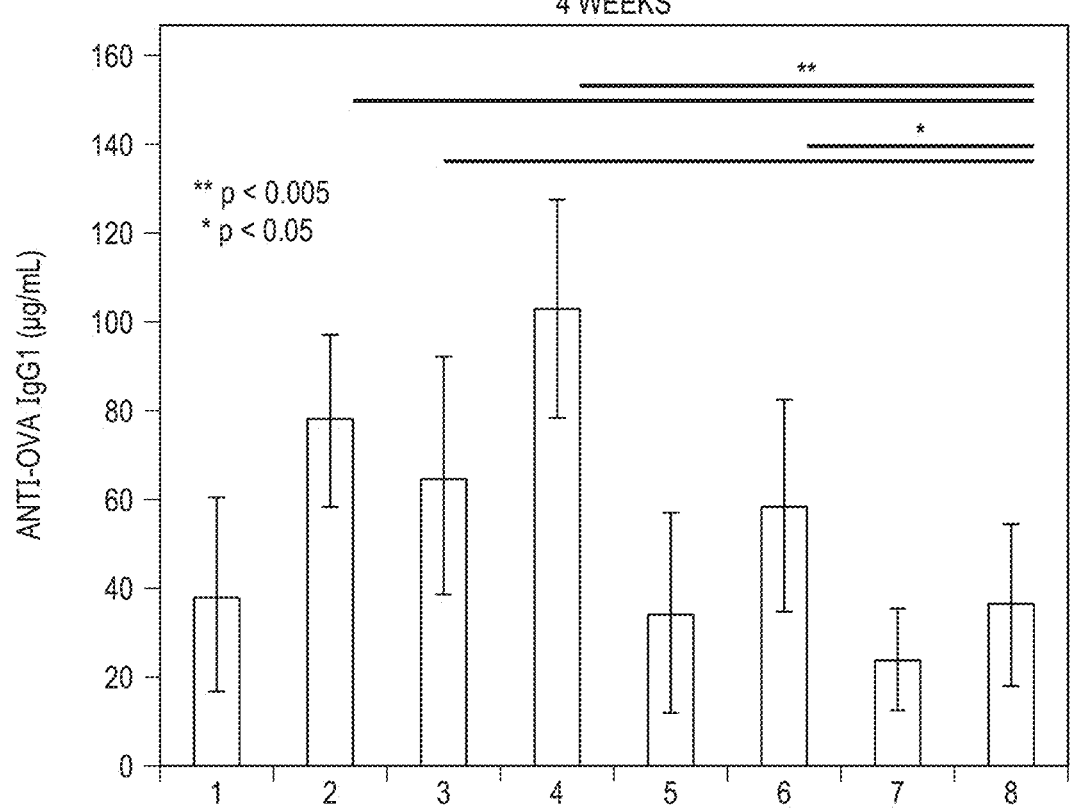

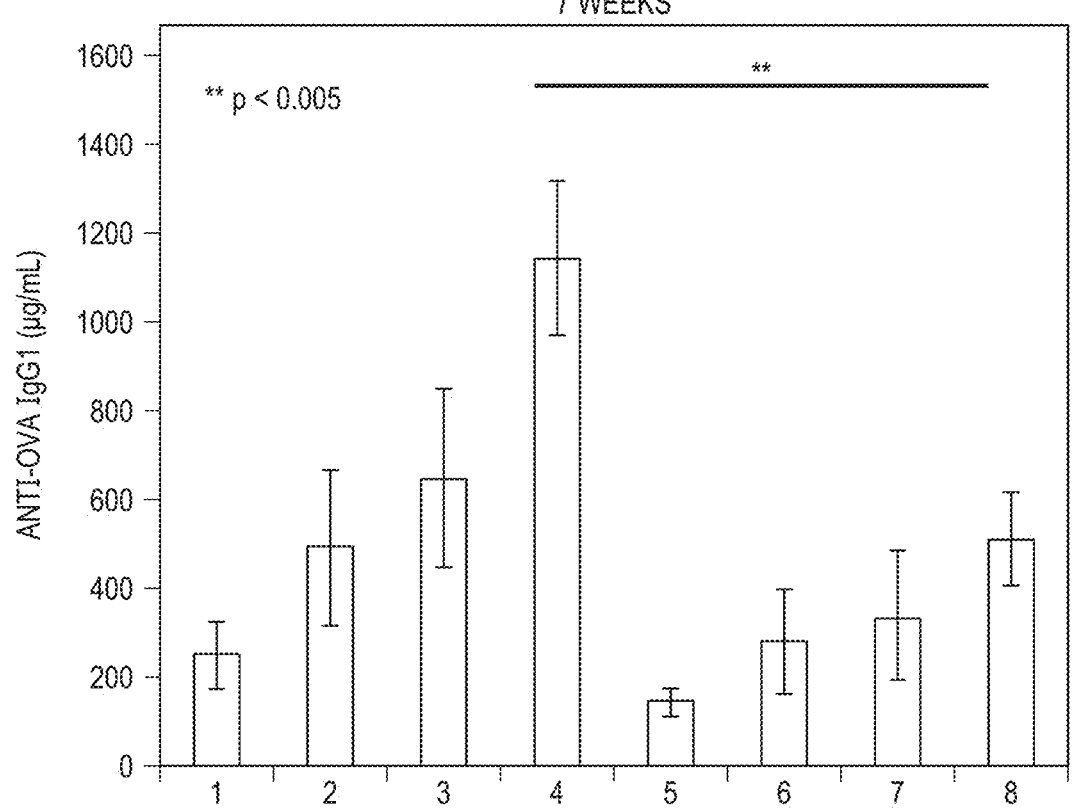

BIODEGRADABLE CATIONIC POLYCARBONATES AS ADJUVANTS FOR VACCINES

BACKGROUND

The present application relates generally to biodegradable cationic polycarbonates as adjuvants for vaccines.

In clinical settings, adjuvants are often incorporated within vaccine formulations through physical or chemical association with antigens. Direct immunization with most antigens will typically lead to a poor immune response and rapid removal of the antigens from the body. Adjuvants are used for several reasons, mainly to enhance immunogenicity, provide antigen-dose sparing, quicken the immune response towards the antigen, prolong the duration of prophylaxis, and thereby reduce the need for booster immunizations. Being immune modulators, adjuvants contribute to the initiation of the innate immune response induced by antigens and can act in various ways in presenting antigens to the immune system.

Adjuvants can act as a depot for the antigen and prolong the duration of which the antigens are presented to the immune cells to increase immune response before the antigens are cleared from the body. As immune modulators, adjuvants can cause inflammatory responses at the delivery site, with mostly localized and transient effects to promote immune cell recruitment and activation. This inflammation can increase vaccine antigen uptake by critical infiltrating cell types and the migration of vaccine-loaded cells to the draining lymph nodes. The activated effectors, such as antigen presenting cells (APCs), process and present the antigens for recognition by certain lymphocytes, such as T cells and B cells, at the draining lymph nodes where they direct the type, magnitude, and quality of the adaptive immune response. When B cells become activated, they can further differentiate into short and long-lived memory B cells and plasma B cells, which produce sustained antibodies against the antigen.

For many decades, there have been only a few adjuvants that are approved for human use by the United States Food and Drug Administration (FDA) including Alum, MF59, virosomes, and montanide ISA 51, despite a plethora of materials being studied for their potential use as adjuvants. These include bacterial cell wall components, nucleic acids, mineral/non-mineral oil, polysaccharides, and polymers. Among the various materials used, the most widely used by far are the particulate adjuvants based on aluminum salt precipitates (Alum). Despite its long use, the mechanisms by which Alum modulates immune response to antigens remain elusive. There are also some limitations of aluminum-based adjuvants, which include localized inflammation, injection site pain and tenderness, and intensification of IgE antibody response, which is an indication for allergic reactions. Other limitations include ineffectiveness for some antigens and incapacity to amplify cell-mediated immune responses in some cases. At the injection sites, aluminum-based adjuvants can cause cell necrosis and induction of inflammation activation and IL1 production and as a result some subjects develop persistent lumps and granulomas at the injection site. Aluminum-based adjuvants can also cause dermatitis to aluminum in some vaccinated subjects, post-immunization headache, arthralgia, and myalgia.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided for formation of a vaccine comprising combining a cationic polymer adjuvant with an antigen to form first immunoparticles through charge interactions. The method further comprises producing a treatment formulation for the vaccine comprising the first immunoparticles.

In another illustrative embodiment, a vaccine comprises immunoparticles formed by combining a cationic polymer adjuvant with an antigen through charge interactions.

In yet another illustrative embodiment, a vaccine comprises first immunoparticles formed by combining a cationic polymer adjuvant with an antigen through charge interactions and second immunoparticles formed by combining the cationic polymer adjuvant with polyinosinic:polycytidylic acid (poly(I:C)).

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIGS. 3A-3D depict size and zeta potential measurement of OVA- and/or poly(I:C)-loaded nano- and micro-complexes in accordance with an illustrative embodiment;

FIG. 4 illustrates in vitro release of antigen in the presence or absence of poly(I:C) in accordance with the illustrative embodiment;

FIGS. 8A-8C illustrate amount of anti-OVA IgG1 present in mouse blood plasma at one-month post-vaccination in accordance with an illustrative embodiment;

FIG. 9 illustrates amount of anti-OVA IgG1 present in mouse blood plasma at nine-month post-vaccination in accordance with an illustrative embodiment;

FIG. 10 shows changes in tumor size as a function of time in accordance with an illustrative embodiment;

FIGS. 11A-11D show in vivo innate immune response at one month post-vaccination in accordance with an illustrative embodiment;

FIG. 12 shows cytotoxic T lymphocyte (CTL) responses of various formulation containing OVA in accordance with an illustrative embodiment;

FIGS. 14A and 14B show vaccination and production of anti-OVA IgG1 in accordance with an illustrative embodiment;

DETAILED DESCRIPTION

Figure 1:
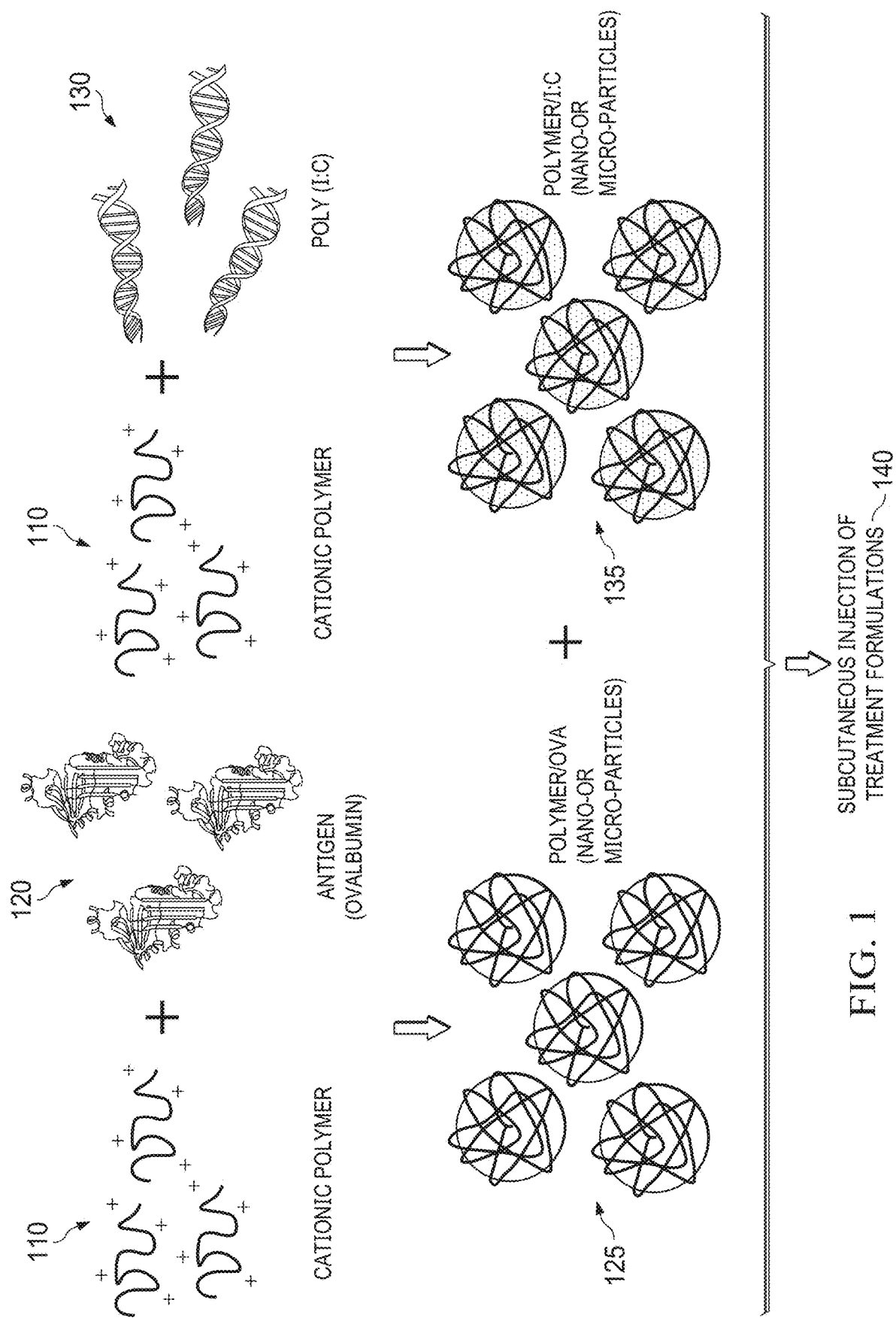
FIG. 1 illustrates formation of immunoparticles through charge interactions in accordance with an illustrative embodiment.

To further improve vaccine formulations with better adjuvants, a considerable amount of effort has been put into discovering alternatives, including synthetic polymers. In recent times, studies have been conducted to develop biocompatible and biodegradable polymers to replace conventional adjuvants. The ability of polymers to act as adjuvants is largely dependent on their extrinsic and intrinsic properties such as polymer structure, amphiphilicity and surface charge display of self-assembled structures. Combination between the polymeric adjuvants and antigens can occur via physical or chemical interactions. The facile manipulation of polymer chemistry will enable the adjuvants to be tailored for the antigen of interest.

Recently, a study has reported a delivery system based on poly(glutamic acid) and cholesterol which form nanoparticles with polyinosinic:polycytidylic acid (poly(I:C)) and ovalbumin (OVA). However, the particles had large polydispersity indices. In another study, amphiphilic pentablock copolymers based on Pluronic F127, poly(ethylene oxide) (PEO) and poly(propylene oxide) (PPO), and cationic blocks such as poly(diethylaminoethyl methacrylate) (PDEAEM) were used as delivery vehicles for OVA. Despite increasing the cellular uptake of the antigens by immune cells, the pentablock copolymer (PBC) micelles did not activate innate immune cells, as exhibited by expression of cell surface markers, and there was less secretion of inflammatory cytokines. Furthermore, these polymers are not biodegradable. Biodegradable polymers such as polyester poly(lactide-co-hydroxymethylglycolic acid) formed spherical nanoparticles (300 to 400 nm) that were able to retain at injection sites for more than 13 days and enable transport of the antigen into the draining lymph nodes.

The adjuvant capacity of polymers is dependent on many factors and the chemical structure of the polymers plays a key role in determining the efficacy of vaccination. In one notable study, non-ionic amphiphilic copolymers comprising polyoxypropylene (POP) and polyoxyethylene (POE) blocks were tested for their potential to induce immunization against bovine serum albumin. The adjuvant activity was lower with a higher amount of hydrophilic POE in the block copolymers. Similarly, in other systems where amphiphilic copolymers were involved, the increase in hydrophobic content correlated with higher immune response. This is probably because the hydrophobic domain of polymers is favorable for protein adsorption, which recruits more primary APCs for phagocytosis of the antigens, thereby increasing the level of interaction and uptake of antigens by the immune cells.

Another interesting point to note is that the choice of adjuvant can affect the isotype of antibody and the nature of the T cells produced. Vaccination strategy is also made more complex as some infections may be more effectively combated by specific antibody isotype. In some cases, T cell responses rather than the vaccine-induced antibodies for some intracellular pathogens such as tuberculosis (TB), tularemia, chlamydia, and leishmaniasis. Thereby, synthetic polymers represent a novel addition to the line of candidate compounds to provide new ways of immunostimulation and can work hand-in-hand with other adjuvants in enhancing vaccination efficacy. In one study, the encapsulation of synthetic human papillomavirus (HPV) peptide antigen in polyester-based nanoparticles resulted in the enhancement of HPV-specific CD8+ T cell population when Poly(I:C) was incorporated. The enhancement of immune response with the delivery of antigen-loaded nanoparticles alongside with Poly(1:C)-containing nanoparticles was also reported in other studies involving chitosan-based polymers and polypeptides.

In accordance with the illustrative embodiments, diblock copolymers containing a polycarbonate (PC) block bearing pendent propyl chloride groups and a poly(lactide) (PLA) block are synthesized by controlled ring-opening polymerization, followed by quaternization of the pendent propyl chloride groups by trimethylamine, to form cationic diblock copolymers. These positively charged polymers are mixed with the model antigen, OVA and poly(I:C) to form micro- or nano-sized particles, which are investigated for their immunostimulatory properties. Non-invasive bioimaging is carried out to visualize the biodistribution of the particles. The adjuvant capacity of the polymers is determined via the quantification of anti-OVA antibodies produced subsequent to administration. Long-term immunity against OVA-expressing tumor cells is studied by challenging the vaccinated subjects with tumor cells at nine months post-vaccination.

In accordance with the illustrative embodiments, biodegradable cationic polycarbonate and polylactide block copolymers are synthesized and successfully used as novel vaccine adjuvants to provide enhanced anticancer immunity. The polymers form nanoparticles with OVA. In vivo experiments show that these particles remain longer in the subcutaneous injection site as compared to OVA alone and led to higher production of anti-OVA specific antibodies with prolonged immunostimulation. When OVA was combined with toll-like receptor 3 agonist poly(I:C) (mRNA) that was either co-entrapped in the same particles or as separate particles, the amount of anti-OVA IgG1 antibodies produced in subjects is higher compared to that in subjects vaccinated with OVA-loaded particles alone. Therapeutic efficacy of cationic polymers-based adjuvants is higher than that of widely used aluminum-based adjuvants. Notably, the cationic polycarbonates are not associated with any adverse in vivo effects. Therefore, these biodegradable polymers are promising substitutes for aluminum-based adjuvants in vaccine formulations.

FIG. 1 illustrates formation of immunoparticles through charge interactions in accordance with an illustrative embodiment. Adjuvant 110 is added to antigen 120, which is ovalbumin in the depicted example. The antigen 120 elicits an immune response. Adjuvant 110 is a substance that enhances the body's immune response to the antigen 120. In accordance with the illustrative embodiment, adjuvant 110 is a cationic polymer. The combined cationic polymer 110 and antigen 120 forms polymer/OVA 125 (nano- or microparticles).

Adjuvant 110 is also added to polyinosinic:polycytidylic acid (poly(I:C)) 130 to form polymer/I:C 135 (nano- or micro-particles). Poly (I:C) 130 is an immunostimulant used in the form of its sodium salt to simulate viral infections. Poly (I:C) is known to interact with toll-like receptor 3 (TLR3), which is expressed at the endosomal membrane of B-cells, macrophages, and dendritic cells.

Polymer/OVA 125 and polymer/I:C 135 are combined to form subcutaneous injection of treatment formulations 140. In accordance with the illustrative embodiment, the resulting subcutaneous injection of treatment formulations 140 are then given to subjects as a vaccination.

The cationic polymer may comprise polycarbonates including quaternary ammonium-functionalized polycarbonates and guanidinium-functionalized polycarbonates. Mannose functional group can be incorporated to increase uptake by immune cells. The antigens include viral membrane proteins (e.g. HBV, HPV, influenza), peptides, RNA, DNA, and deactivated virus particles.

Materials and Methods

Materials 1,8-Diazabicyclo[5.4.0]undec-7-enc (DBU; 98%) is stirred over CaH2, vacuum distilled twice, and then stored in a glove box. The cyclic carbonate monomer bearing a propyl chloride group (MTC-PrCl) and N-(3,5-trifluoromethyl)phenyl-N'-cyclohexylthiourea (TU) are prepared according to previous protocols. They are freeze-dried under high vacuum before being transferred to the glove box. Murine lymphoma cell lines E.G7-OVA and rat alveolar macrophage NR8383 cell line are cultured in RPM11640 supplemented with 10% fetal calf serum, 100 U/ml penicillin and 100 µg/ml streptomycin (HyClone, U.S.A.). 2-Mercaptoethanol (ME, 50 µM) is added in the culture medium for E.G7-OVA.

Polymer Synthesis

Synthesis of 4-MBA-P(MTC-PrCl)30-PLA25

In a glovebox, 4-methylbenzyl alcohol (4-MBA, 6.22 mg, 0.05 mmol), MTC-PrCl (0.284 g, 1.2 mmol) and TU (37 mg, 0.1 mmol) are dissolved in 1.5 mL of dry DCM in a 20 mL of vial, followed by addition of DBU (15 µL, 0.1 mmol) to initiate the polymerization. After reacted for 3.5 hours, L-Lactide (L-LA, 0.108 g, 0.75 mmol) in 0.75 mL of dry DCM solution is added and the reaction continued for another 2.5 h before being quenched using benzoic acid. The reaction solution precipitated in cold MeOH, centrifuged, washed three times with cold MeOH and dried in vacuo, yielding 4-MBA-P(MTC-PrCl)$_{30}$-PLA$_{25}$ as white powder (Yield, 86%). PDI: 1.23. $^1$H NMR (400 MHz, CDCl$_3$, 22° C.): δ 5.16 (m, br, 25H, —CH— of PLLA), 4.29 (m, 180H, —CH$_2$— of MTC backbone and —OCH$_2$— of PrCl), 3.60 (t, 60H, —CH$_2$Cl— of PrCl), 2.35 (s, 3H, —PhCH$_3$ of 4-MBA), 2.10 (s, 60H, —CH$_2$— of PrCl), 1.58 (m, 75H, —CH$_3$ of PLLA), 1.27 (s, 90H, —CH$_3$ of MTC).

Similarly, 4-MBA-P(MTC-PrCl)$_{17}$-PLA$_{10}$ is synthesized. Yield, 75%; PDI: 1.29. $^1$H NMR (400 MHz, CDCl$_3$, 22° C.): δ 5.11 (m, br, 10H, —CH— of PLLA), 4.29 (m, 102H, —CH$_2$— of MTC backbone and —OCH$_2$— of PrCl), 3.60 (t, 34H, —CH$_2$Cl— of PrCl), 2.34 (s, 3H, —PhCH$_3$ of 4-MBA), 2.10 (s, 34H, —CH$_2$— of PrCl), 1.54 (m, 30H, —CH$_3$ of PLLA), 1.27 (s, 51H, —CH$_3$ of MTC).

Synthesis of PN30-PLA25

PN30-PLA25 is synthesized by quaternation of 4-MBA-P(MTC-PrCl)30-PLLA25 using trimethylamine (TMA) as the quaternation agent. Briefly, in a 60 mL of pressure safe Schlenk tube, 4-MBA-P(MTC-PrCl)30-PLLA25 (0.33 g, 1.1 mmol of PrCl groups) is dissolved in 20 mL of dry ACN. Due to the gaseous nature of TMA at room temperature, the Schlenk tube and TMA bottle are cooled in dry ice bath for 20 min, and then a great excess amount of TMA (1 mL, about 10 equiv of PrCl groups) is added to the polymer solution and the tube is sealed. The reaction solution is heated to 50° C. for two days. Abler quaternization, the solution is concentrated to dryness, and the residue is subjected to purification via dialysis against a 1:1 acetonitrile/2-propanol solvent mixture in a dialysis bag with molecular weight cut-off of 1 kDa. Finally, the solvents are removed, and the resultant polymer freeze dried to yield PN30-PLLA25 as white solid (Yield, 91%). $^1$H NMR (400 MHz, DMSO-d$_6$, 22° C.): δ 5.21 (m, br, 25H, —CH— of PLLA), 4.20 (d, 180H, —CH2- of MTC backbone and —OCH$_2$— of —PrN$^⊕$(CH$_3$)$_3$), 3.47 (s, br, 60H, —CH$_2$N$^⊕$—), 3.14 (s, 270H, —N$^⊕$(CH$_3$)$_3$), 2.32 (s, 3H, —PhCH$_3$ of 4-MBA), 2.05 (s, 60H, —OCH$_2$CH$_2$CH$_2$N$^⊕$—), 1.46 (m, 75H, —CH$_3$ of PLLA), 1.21 (s, 90H, —CH$_3$ of MTC).

Polymer Characterization

Gel Permeation Chromatography (GPC) of Polymers

GPC analysis for the diblock copolymers before quaternization is carried out with a Waters HPLC system consisting of a 2690D separation module, two Styragel HR1 and HR4E (THF) 5 µm columns (300×7.8 mm) in series and an Optilab rEX differential refractometer (Wyatt Technology Corporation, USA) detector. THF is used as eluent at a flow rate of 1 mL/min at 35° C. Number-average molecular weights (Mn) and polydispersity indices (PD1) are obtained from a calibration curve of a series of monodispersed polystyrene (PS) standards (Molecular weights of the highest peak range from 360 to 778,000 Da, Polymer Standard Service, U.S.A.).

$^1$H-NMR spectra of the diblock polycarbonates and the cationic polycarbonates are recorded on a Bruker Advance 400 NMR spectrometer (400 MHz) under the conditions of ambient temperature, an acquisition time of 3.2 s, a pulse repetition time of 2.0 s, a 300 pulse width, 5208-Hz spectral width, and 32 K data points. Chemical shifts are referenced based on the respective solvent peaks (δ=7.26 ppm for CDCl3 and 2.50 ppm for DMSO-d6).

Formation of Vaccine-Loaded Nano- and Micro-Particles

To generate the complexes between cationic polymer, OVA and/or Poly (I:C), the negatively charged components, OVA (1 mg/mL) and poly (I:C) (1 mg/mL) are first dissolved in HPLC grade water, and this solution is then added to the polymer solution (in HPLC water) at equivalent volumes. The mixtures are then left to stand at room temperature for 30 min to form a stable complex. The particles are characterized with respect to their size and zeta potential using a Zetasizer with dynamic light scattering capability (scattering angle: 90°) and equipped with a He—Ne laser beam at 658 nm (Malvern Instruments Zetasizer Nano ZS, UK).

In Vitro Release of OVA from Polymeric Particles

To quantify the in vitro release of OVA from the OVA-containing polymeric particles, the samples are first prepared at polymer:OVA molar ratio of 16:1 with and without Poly(I:C). The samples (0.5 mL) are then mixed with PBS (0.5 mL) (pH 7.4) and kept at 37° C. At designated time points, the samples are centrifuged at 20,000×g, 24° C. for 10 min, and 700 µL of the supernatant is removed and replaced with fresh medium (PBS). The amount of free OVA in the supernatant is then determined using BCA assay (Thermofisher, U.S.A.).

Biodistribution of OVA-Loaded Polymeric Particles

To evaluate the biodistribution of nanocomplexes, OVA is labeled using Alexa Fluor 750 succinimidyl ester and Poly (1:C) was first modified with 5' EndTag™ Labeling DNA/RNA Kit (Vector Labs, U.S.A.) and labeled using Alexa Fluor 750 maleimide according to the manufacturer's manual. Female balb/c mice, weighing 20-25 g are randomly divided into two groups, one being OVA-loaded complexes and the other OVA alone. The mice are injected with 200 μL of the OVA-loaded complexes or OVA alone (dosage: 100 μg OVA) subcutaneously at their right flank. The mice are sacrificed at 0.5, 3, 24 and 48 h post administration, and organs including lymph node, heart, liver, spleen, lungs, kidneys and skin tissue at the injection site are excised and imaged using IVIS (Caliper Life Science, U.S.A.). All animal experiments are conducted in accordance with the approved protocol from the Institutional Animal Care and Use Committee (IACUC) at the Biological Resource Centre of Singapore.

Detection of Mouse IL-6, TNF-α and Anti-OVA $IgG_1$ in Plasma Via ELISA

Female C57BL/6 mice weighing an average of 20-25 g are injected subcutaneously with 200 μL of solution containing 0.5 mg/mL of OVA in the presence and absence of cationic polymers. In some formulations, poly(I:C) is mixed with OVA. At various time points, whole blood is collected from the mice via cardiac puncture. The blood samples are then centrifuged at 1000×g for 10 min at 4° C. and the supernatant (plasma) is then stored at −80° C. prior to ELISA analysis. ELISA is performed using mouse IL-6 (Abcam, England), TNF-α (Abcam, England) and anti-OVA IgG1 ELISA quantification set (Cayman Chemical, U.S.A.) according to the manufacturer's protocol. To evaluate the differences in the mouse cytokines and antibodies concentration in plasma between different formulations, two-tailed Student's t-test is performed. P50.05 indicates a statistically significant difference.

Cytokine Release from Splenocytes

Female C57BL/6 mice weighing an average of 20-25 g are injected subcutaneously with 200 μL of solution containing 0.5 mg/mL of OVA in the presence and absence of cationic polymers. In some formulations, poly(I:C) is mixed with OVA. At Day 28 post-immunization, the mice are sacrificed, and the spleens are aseptically removed and red blood cells-depleted splenocytes are prepared. The splenocytes are re-stimulated in vitro with OVA (1 mg/mL), in RPMI1640 medium supplemented with 10% FBS and antibiotics. 48 hours later, supernatant of the splenocyte culture are collected and stored at −80° C. prior to ELISA analysis. ELISA is performed using mouse IL-6 (Abcam, England), TNF-α (Abcam, England) according to the manufacturer's protocol. The experiment is performed with four replicates. Statistical significance in difference is evaluated by Student's T-Test and P≤0.05 is considered statistically significant. Data reported are average f standard error of the mean values.

Cytotoxicity Test on NR8383

Rat alveolar macrophage NR8383 cells are seeded at a density of $3×10^4$ cells per well onto a 96-well plate and incubated overnight at 37° C. To treat the cells, the spent medium is removed and 100 μL of fresh medium containing various immunization formulations with 10 μg of OVA and/or 10 μg of Poly(I:C) are added to each well. Subsequently, the cells are incubated for 24 h at 37° C. Reagents from the CellTiter 96@ AQueous One Solution Cell Proliferation Assay Kit (Promega, U.S.A.) and cell culture medium are mixed at 1:4 volume ratio, and 100 μL of this mixture is then added to each well. Subsequently, the cells are left to incubate for 2 h at 37° C. in the dark and the absorbance at 490 nm is measured. Untreated cells are used as the control, and the absorbance readings are then expressed as a percentage of the cell viability of the control. The experiment is performed with four replicates. Statistical significance in difference is evaluated by Student's T-Test, and P50.01 is considered statistically significant. Data reported are average±standard error of the mean values.

Cellular Uptake of Nanoparticles

Flow cytometry: Bone marrow derived dendritic cells (BMDC) or bone marrow derived macrophages (BMDM) are seeded on a 12-well plate at $3×10^6$ cells/well (1 mL). Alexa Fluor 488 labeled OVA (AF488-OVA) (25 μg/mL) or Alexa Fluor 594 labeled Poly(1:C) (AF594-I:C) (10 μg/mL) are added to the cells either as free form or nanocomplexes with PN17-PLLA10 at mole ratio of 16:1 for Alexa Fluor 488 labeled OVA (AF488-OVA) or mass ratio of 2.5:1 for AF594-I:C respectively. The cells are incubated for 3 hours at 37 FIC in a 5% $CO_2$ incubator. The cells are detached from the plates by incubating them with 0.5 mL of non-enzymatic cell dissociation buffer (Biological Industries, Israel) for 5 min at 37□C. The cells are then washed twice with 1×PBS and resuspended in 1×PBS containing 5% FBS. The population of fluorescent cells are analyzed using BD LSRII analyzer, U.S.A. The experiment is performed in triplicates. Statistical significance in difference is evaluated by Student's T-Test, and P≤0.01 is considered statistically significant. Data reported are average±standard error of the mean values.

Confocal microscopy: Bone marrow derived dendritic cells (BMDC) or bone marrow derived macrophages (BMDM) are seeded on 2-well Nunc Lab-Tek II CC2 Chamber Slide System (polylysine-coated) (Nunc, U.S.A.) at $5×10^5$ cells/well (1.2 mL). AF488-OVA (25 μg/mL) or AF594-I:C (10 μg/mL) are added to the cells either as free form or nanocomplexes with PN17-PLLA10 at mole ratio of 16:1 for AF488-OVA or mass ratio of 2.5:1 for AF594-I:C, respectively. The cells are incubated for 3 hours at 37□C in a 5% CO2 incubator. The cells are then washed twice with 1×PBS and fixed with 10% neutral buffered formalin for 10 min. The cells are then washed twice again with 1×PBS and Prolong Gold with DAPI (Thermofisher, U.S.A.) added as the mounting medium. Imaging is performed using confocal microscope FV3000 (Olympus, Japan).

Localization of Nanoparticles in Lymph Nodes

The localization of OVA and Pol(I:C)-loaded nanoparticles is analyzed after dissection of the mesenteric and inguinal lymph nodes, 30 min post administration of PN17-PLLA10 nanoparticles containing 50 μg of AF488-OVA or 50 μg of AF594-I:C. The lymph nodes are prepared via cryosectioning and viewed using FV3000 confocal microscope (Olympus, Japan).

Long-Term Immunity Against OVA-Expressing Tumor Cells

Female C57BL/6 mice weighing an average of 20-25 g are injected subcutaneously with 200 μL of solution containing 0.5 mg/mL of OVA in the presence and absence of cationic polymers. In some formulations, poly(I:C) is mixed with OVA. At 9 months post-immunization, murine lymphoma E.G7-OVA cells are propagated in the mice by subcutaneous inoculation of $5×10^6$ in vitro-cultured cells in 200 μL of a cell suspension (1:1 with Geltrex (Thermofisher, U.S.A.)). Subsequently, the tumors are measured by calipers in two orthogonal diameters, and the volumes are calculated as $L×W^2/2$, where L and W are the major and minor diameters respectively. Statistical significance in difference is evaluated by Student's T-Test, and P≤0.05 is considered statistically significant. Data reported are average±standard error of the mean values.

Cytotoxic T Lymphocyte Induction and Assay Following Vaccination with OVA Formulations Female C57BL/6 mice weighing an average of 20-25 g are injected subcutaneously with 200 μL of solution containing 0.5 mg/mL of OVA in the presence and absence of cationic polymers. In some formulations, poly(I:C) is mixed with OVA. At Day 28 post-immunization, the mice are sacrificed, and the spleens are aseptically removed and red blood cells-depleted splenocytes are prepared. The splenocytes are re-stimulated in vitro with OVA (1 mg/mL), in RPMI1640 medium supplemented with 10% FBS and antibiotics. 18 hours later, the splenocytes are collected and used as effector cells at an effector:target of 50:1 1 ($2.5 \times 10^6$: $5 \times 10^4$ per well in 96-well plate). Target cells used were EG.7-OVA and cytolytic activity was determined 4 hours later by performing the CytoTox 96 Non-Radioactive Cytotoxicity Assay (Promega, U.S.A.). The experiment was performed with 4 replicates. Statistical significance in difference was evaluated by Student's T-Test and P≤0.05 was considered statistically significant. Data reported are average±standard error of the mean values.

Results and Discussion

Polymer Synthesis and Characterization

Figure 2A:
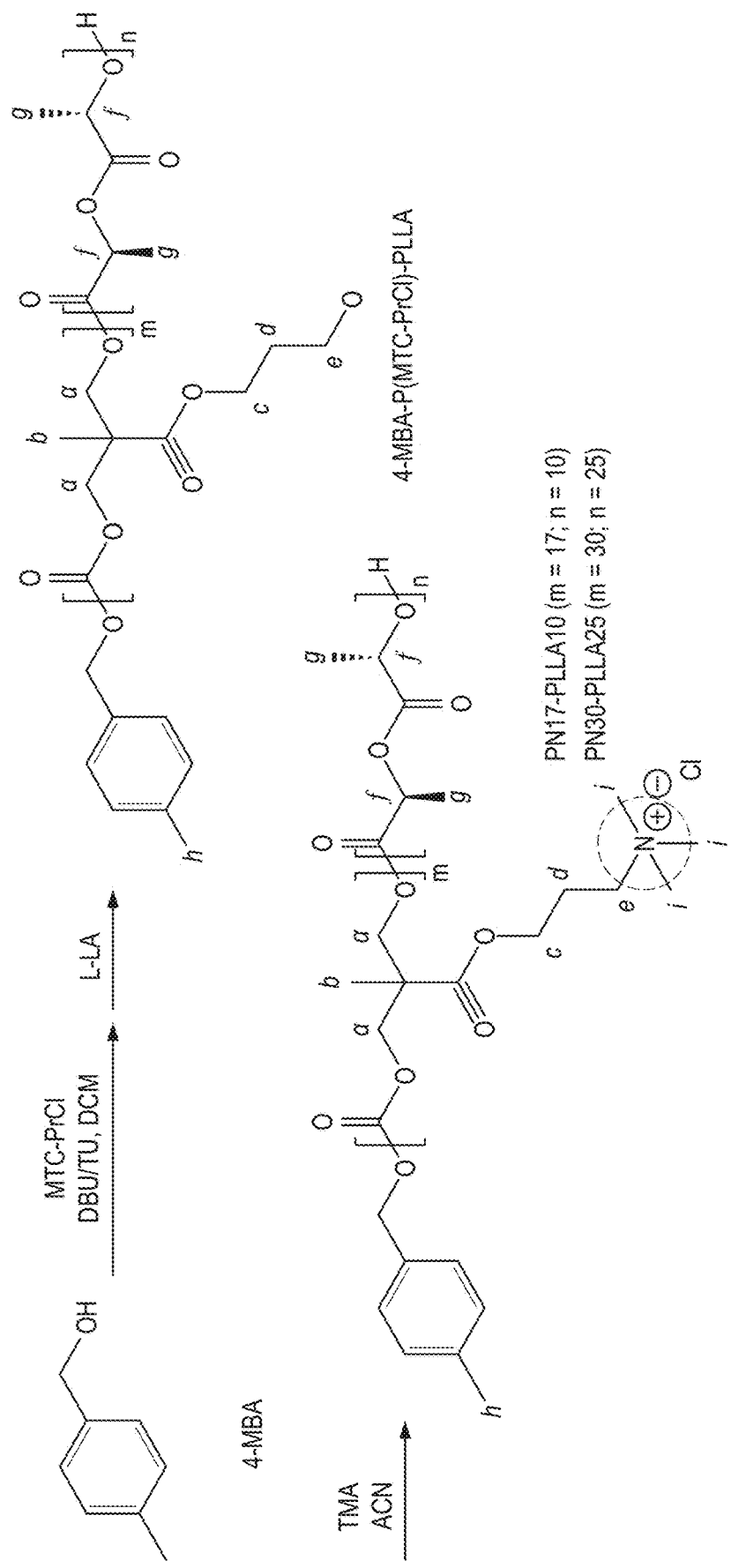
FIG. 2 illustrates the chemical structure and synthetic procedures of the cationic diblock copolymers in accordance with an illustrative embodiment.
Figure 2B:
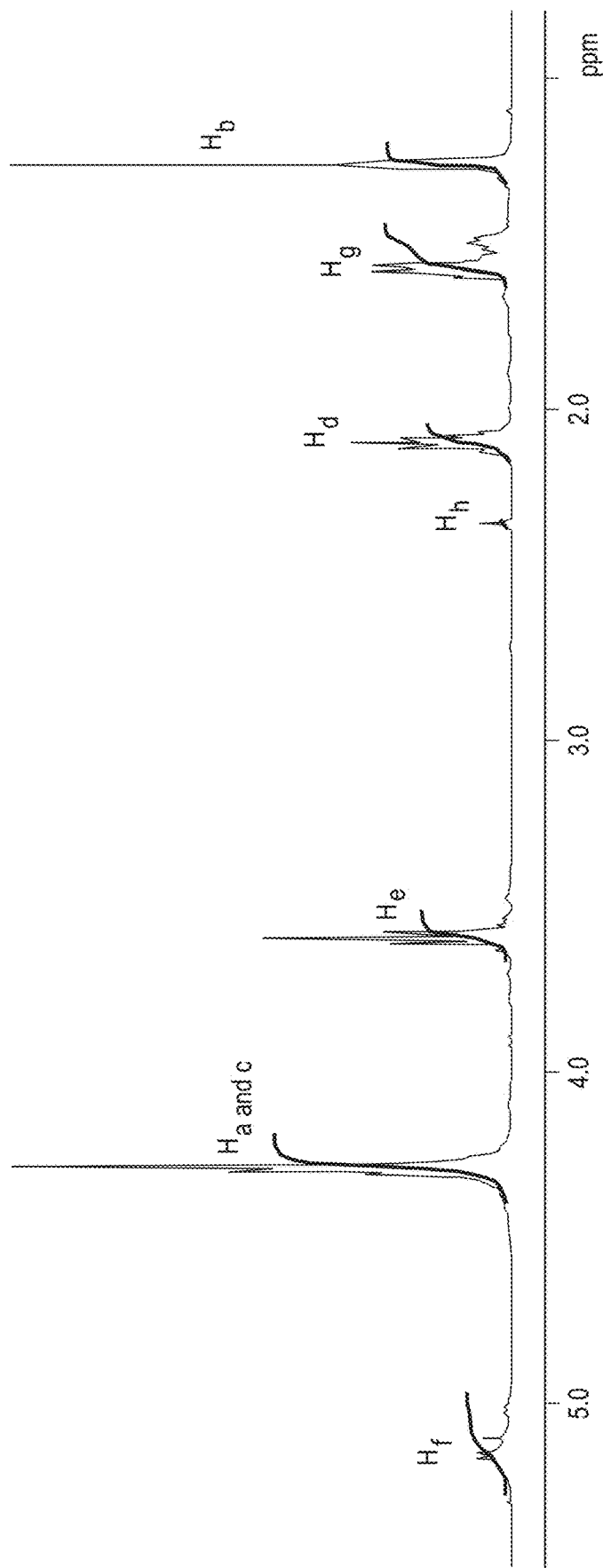
Figure 2C:
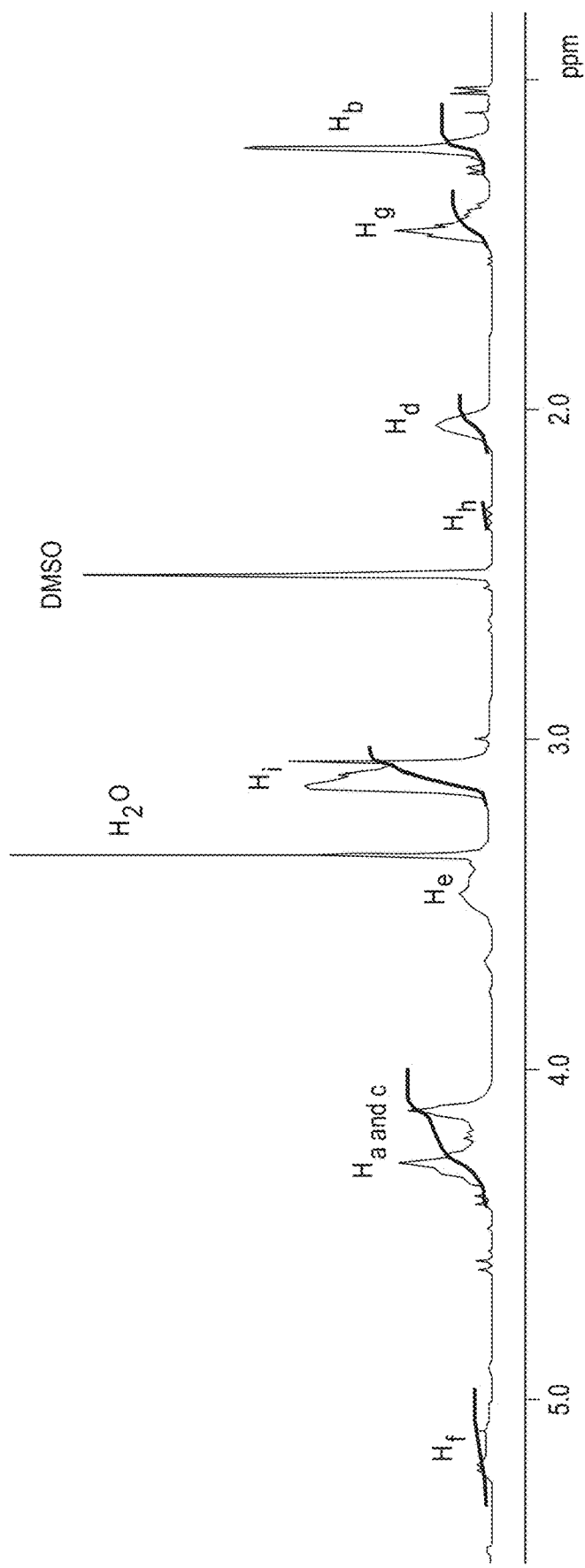

The cationic diblock copolymers are synthesized by sequential copolymerization of a cyclic carbonate monomer containing a pendent propyl chloride group (MTC-PrCl) with L-lactide (L-LA) using 4-methylbenzyl alcohol (4-MBA) as the initiator, and DBU and TU as co-catalysts to facilitate ring-opening polymerization (ROP). FIG. 2 illustrates the chemical structure and synthetic procedures of the cationic diblock copolymers in accordance with an illustrative embodiment. FIG. 2(*a*) illustrates the chemical structure of the cationic deblock copolymers. Then, ammonium quaternization of the PrCl groups on the carbonate block with trimethylamine (TMA) generated the cationic diblock copolymers. The compositions of the precursor block copolymers were estimated from $^1$H NMR spectroscopy by quantitative comparisons between integral intensities of the peaks of methylene groups of PrCl at 2.05 ppm and the methyl hydrogens of L-LA at 1.46 ppm with that of methyl protons of 4-MBA at 2.35 ppm. FIG. 2(*b*) depicts quantitative comparisons between integral intensities of the peaks for $^1$H NMR of 4-MBA-P(MTC-PrCl)$_{30}$-PLLA$_{25}$ in CDCl$_3$.

There are 30 MTC-PrCl and 25 L-LA units in the polymer 4-MBA-P(MTC-PrCl)$_{30}$-PLLA$_{25}$ and 17 MTC-PrCl and 10 L-LA units in the shorter polymer 4-MBA-P(MTC-PrCl)$_{17}$-PLLA$_{10}$. GPC results show that both diblock copolymers have a narrow molecular weight distribution with a PDI value of 1.23 and 1.29, respectively. After ammonium quaternization, both precursor polymers are protonated by TMA, giving the corresponding final cationic diblock copolymer PN$_{30}$-PLLA$_{25}$ and PN$_{17}$-PLLA$_{10}$. FIG. 2(*c*) depicts quantitative comparisons between integral intensities of the peaks for $^1$H NMR of PN30-PLLA25 in DMSO-d$_6$. In proton NMR spectrum of PN30-PLLA25, the newly emerged peak at 3.14 ppm can be attributed to the methyl groups adjacent to quatenary amines from TMA. By comparing their integral intensities with that of methyl protons of 4-MBA at 2.32 ppm, the carbonate unit number of the cationic polymer resembles that of its precursor, indicating a complete quaternization of MTC-PrCl units.

Size and Zeta Potential Measurement

In the absence of negatively charge components, the cationic polymers PN17-PLLA10 and PN30-PLLA25 have size of 174±6 nm (PDI 0.22±0.02) and 157±4 nm (PDI 0.19±0.01), respectively, and zeta potential of 66.0±0.3 mV and 50.6±0.7 mV, respectively. Complexation between cationic PLLA, OVA and/or poly(I:C) show wide variation regarding size and zeta potential of the complexes. When OVA is complexed with the cationic polymer in the absence of poly(I:C), the particles are in nano-size range (between 49 to 155 nm) (Table 1A and B). At higher polymer to OVA ratios (8:1 to 32:1), the polymer with lower molecular weight (PN17-PLLA10) form particles that have smaller average size compared to those with higher molecular weight counterpart (PN30-PLLA25). Particles formed between PN17-PLLA10 and OVA also have lower positive charge compared to those formed using the more cationic PN30-PLLA25, especially at the higher polymer to OVA ratios. Lesser cationicity could confer higher compatibility with the physiological environment and lesser undesirable side effects. Therefore, PN17-PLLA10 is selected for further studies.

Figures 3D, 4:
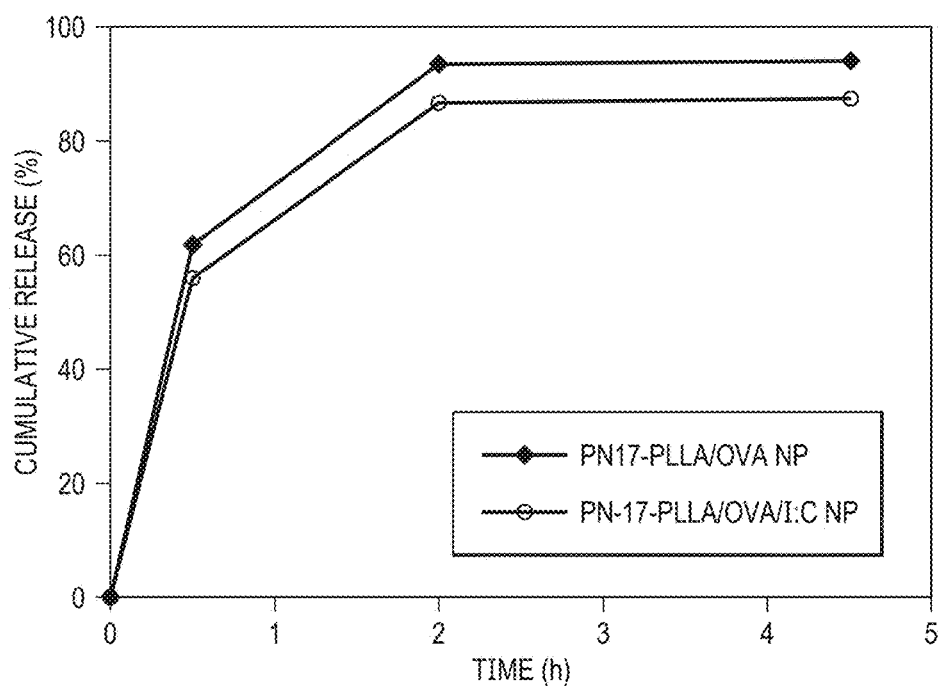

FIGS. 3A-3D depict size and zeta potential measurement of OVA- and/or poly(I:C)-loaded nano- and micro-complexes in accordance with an illustrative embodiment. The concentrations of OVA and poly(I:C) used are 0.5 mg/mL each. When poly(I:C) is complexed with PN17-PLLA10 in the absence of OVA, the size of the particles is smaller than that of the particles with OVA, as shown in FIG. 3C. This is probably because of the greater negative charge present on poly(I:C) (−35.8±5.8 mV) as compared to OVA (−18.1±0.5 mV) that resulted in greater electrostatic attraction between the polymer and poly(I:C). Furthermore, when poly(I:C) and OVA are added together to form complexes with PN17-PLLA10, charge neutralization and steric effects result in larger particle sizes (microparticles) especially at the higher polymer to OVA ratios (8:1 to 32:1).

In Vitro Release of OVA from Nanoparticles

FIG. 4 illustrates in vitro release of antigen in the presence or absence of poly(I:C) in accordance with the illustrative embodiment. In vitro release of OVA from PN17-PLLA10 particles in the presence or absence of poly(I:C) at polymer.OVA molar ratio 16:1 in PBS (pH 7.4), 37° C. The results indicate that OVA can be released out from the particles to stimulate immune response. The in vitro release of OVA from PN17-PLLA10 nanoparticles is studied via the centrifugal method where the OVA-loaded nanoparticles are separated from the released OVA through high speed centrifugation. Most of the OVA (>80%) is released from the nanoparticles in a considerably short time frame of 2 hours. The release of OVA was more rapid for PN17-PLLA10/OVA nanoparticles as compared to PN17-PLLA10/OVA/I:C, possibly due to greater interactions between OVA and poly(I:C) and PN17-PLLA10 in the latter formulation.

Biodistribution of OVA-Loaded Nanoparticles

Figure 5:
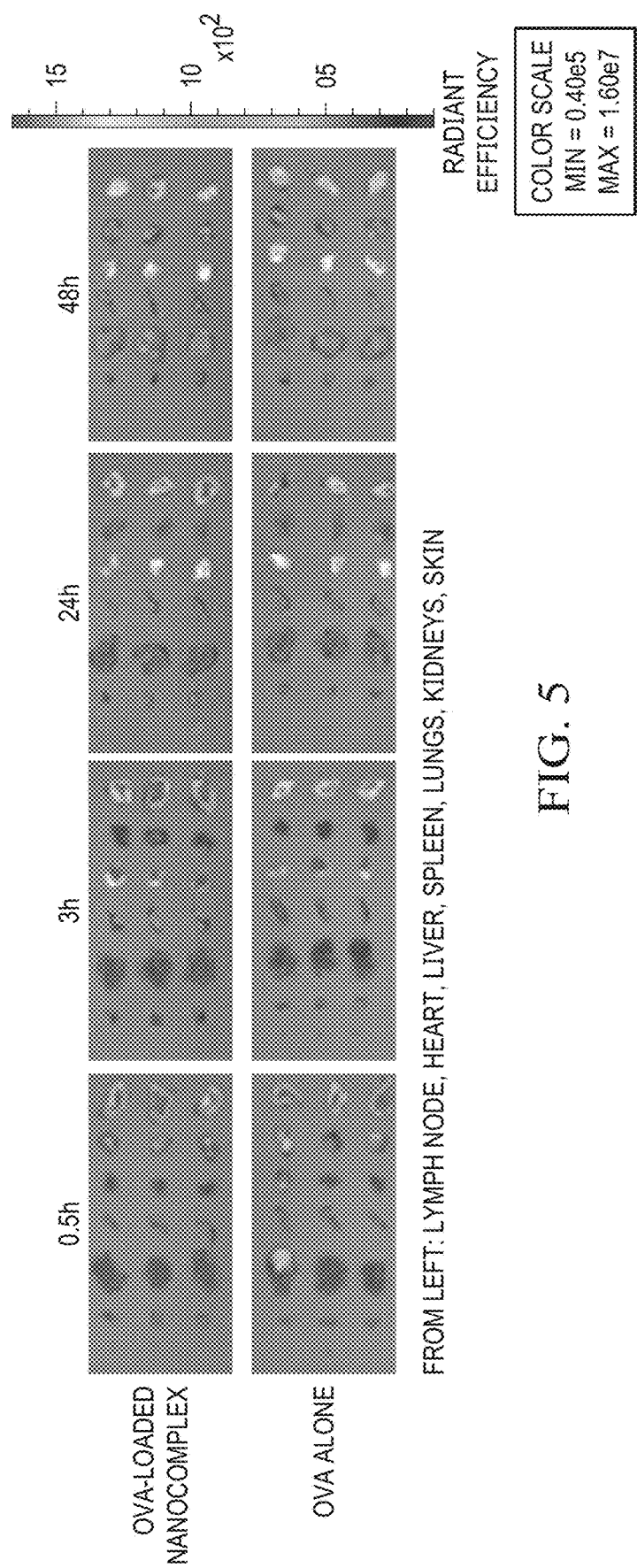
FIG. 5 illustrates biodistribution of Alexa Fluor 750-labeled OVA-loaded nanocomplexes and OVA alone in mice in accordance with an illustrative embodiment.

Biodistribution studies are carried out after the administration of Alexa Fluor 750-labeled PN17-PLLA10/OVA (16:1) nanoparticles and OVA alone. The degree of labeling for OVA was 4.5 mole dye per mole OVA. The mice are sacrificed at 0.5, 3, 24 and 48 hours, and organs are excised to provide a semi-quantitative estimation of the biodistribution of OVA in individual tissues. FIG. 5 illustrates biodistribution of Alexa Fluor 750-labeled OVA-loaded nanocomplexes and OVA alone in mice in accordance with an illustrative embodiment. Mice are sacrificed and organs were excised at 0.5, 3, 24 and 48 hours post administration. As shown in FIG. 5, the biodistribution of the nanocomplexes and OVA alone is similar, except that the amount of OVA-loaded nanocomplexes present at the site of injection is higher compared to the OVA alone at all the time points. Thereby, this could prolong the duration for immunostimulation to occur at nearby non-lymphoid tissue.

Localization of OVA and Poly(I:C)-Loaded Particles in Draining Lymph Nodes

Figure 6A:
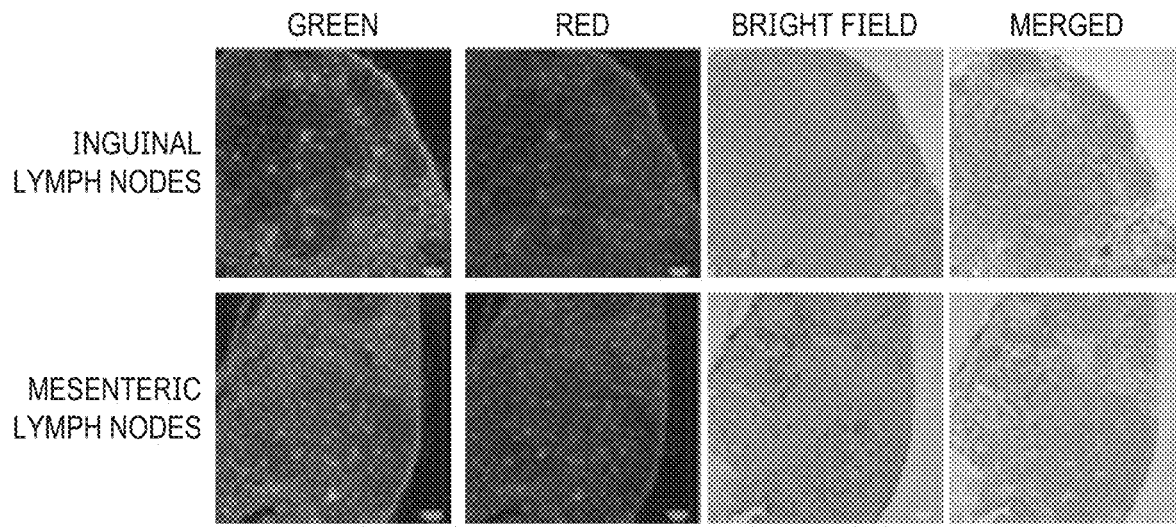
FIGS. 6A-6D illustrate confocal microscopy images of dissected lymph nodes in accordance with an illustrative embodiment.
Figure 6B:
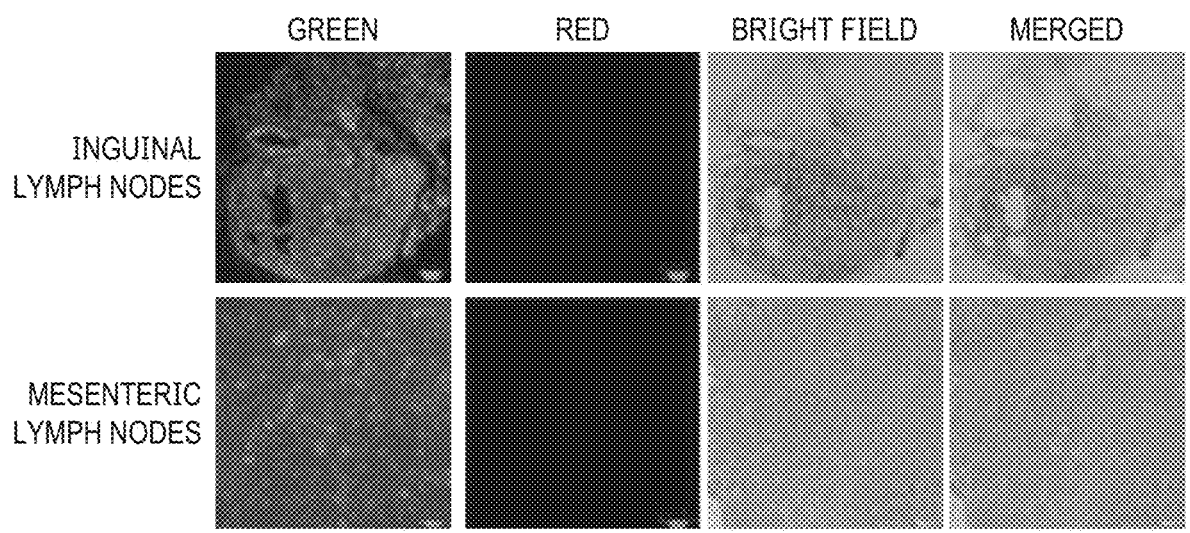
Figure 6C:
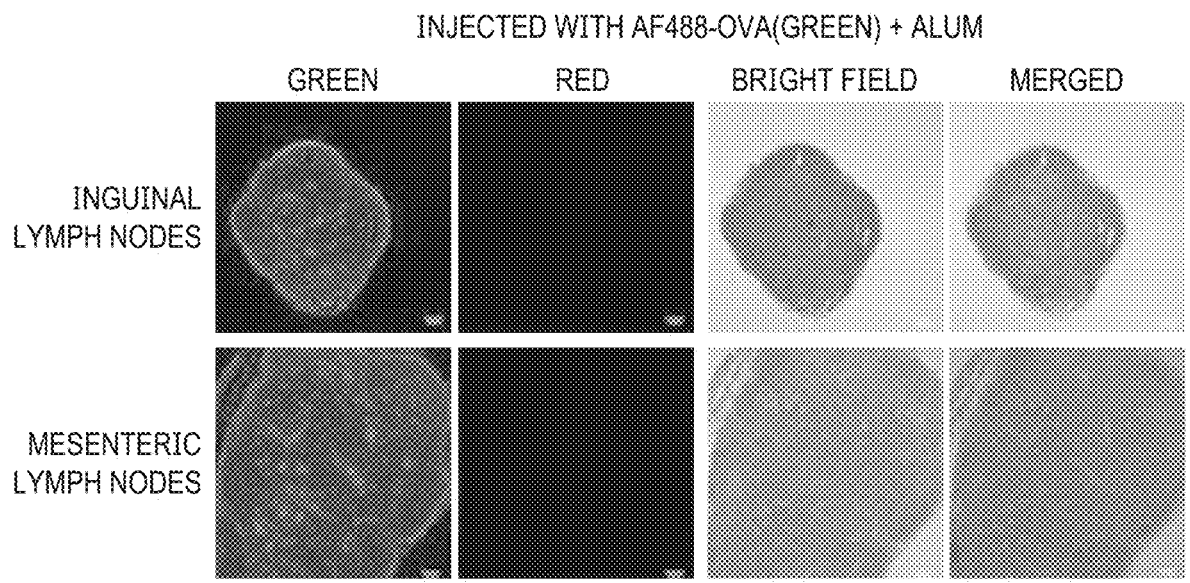
Figure 6D:
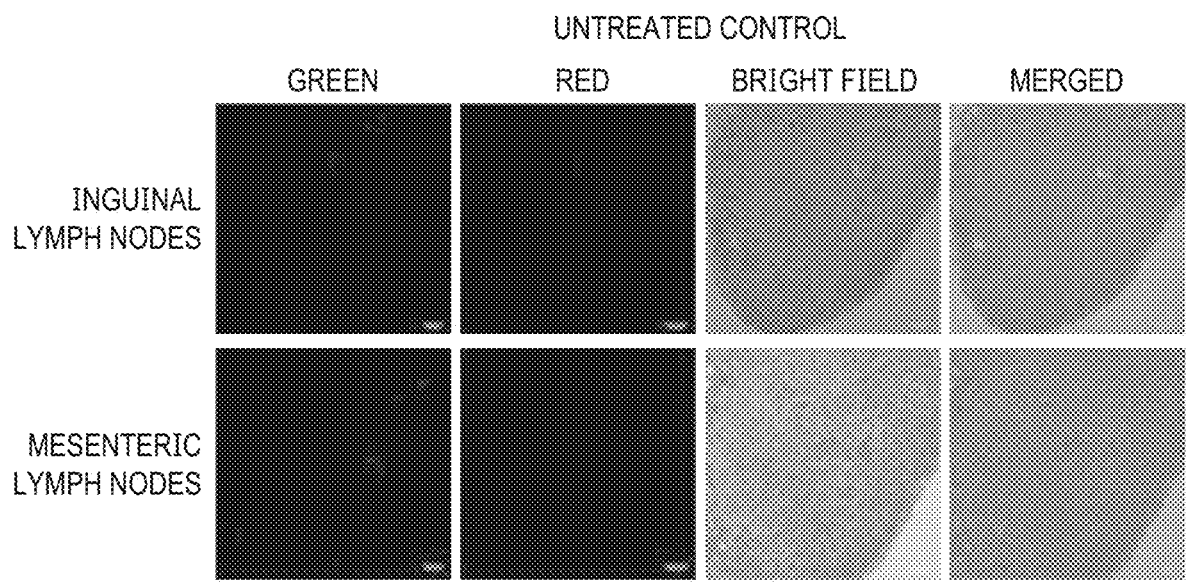

The activation of T cells by antigen-presenting cells (APCs) in lymph nodes (LNs) is a key initiating event in many immune responses. Circulating APCs such as dendritic cells, macrophages, and B cells can process a protein antigen and then migrate to secondary lymphoid organs and present the antigens to T cells, thereby initiating antigen-specific immune responses, or immunological tolerance. FIGS. 6A-6D illustrate confocal microscopy images of dissected lymph nodes in accordance with an illustrative embodiment. FIGS. 6A-6D illustrate images of dissected lymph nodes from mice injected with (A) PN17-PLLA10/AF488-OVA and PN17-PLLA10/AF594-I:C, (B) AF488-OVA, (C) AF488-OVA+Alum and (D) untreated control. Green, red, bright field channels and merged images of all channels are indicated. Scale bar represents 100 µm. FIG. 6A shows the localization of PN17-PLLA10/AF488-OVA and PN17-PLLA10/AF594-I:C in the draining lymph nodes delivery via subcutaneous administration. The presence of both AF488-OVA and AF594-Poly(I:C) in both the representative lymph nodes (inguinal and mesenteric) shows that both the antigens and adjuvants are successfully delivered to lymph nodes at different locations from the injection site (back of the mouse).

Cellular Uptake of Nanocomplexes

Figure 7A:
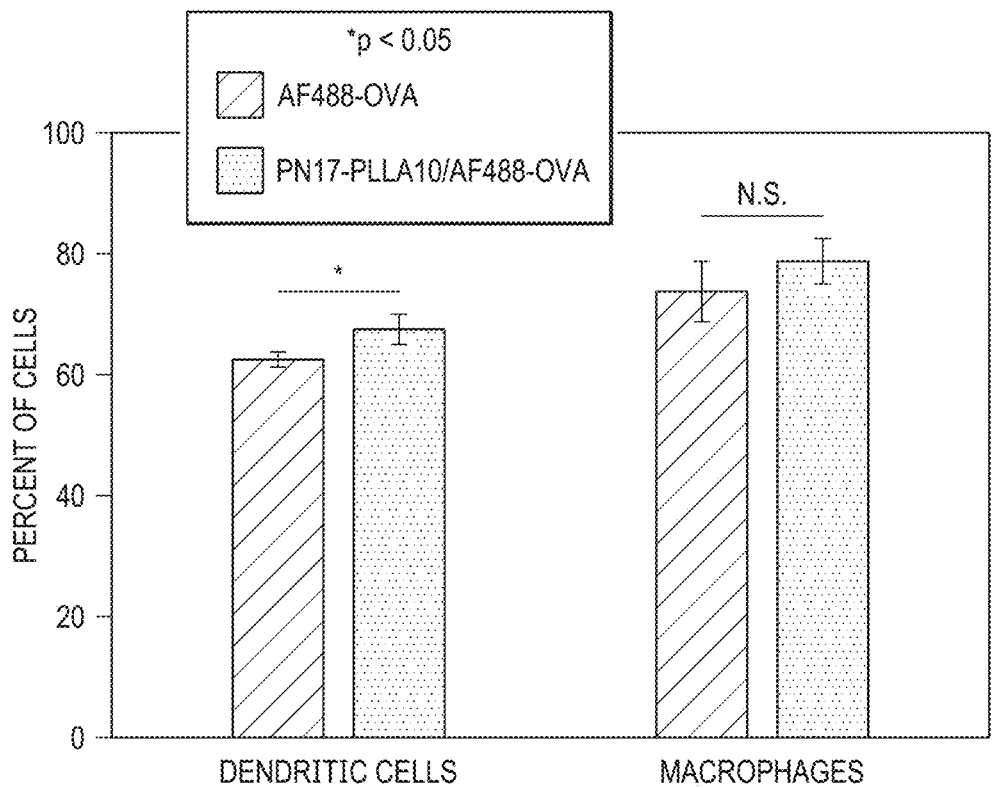
FIGS. 7A-7C illustrate cellular uptake in accordance with an illustrative embodiment.
Figure 7B:
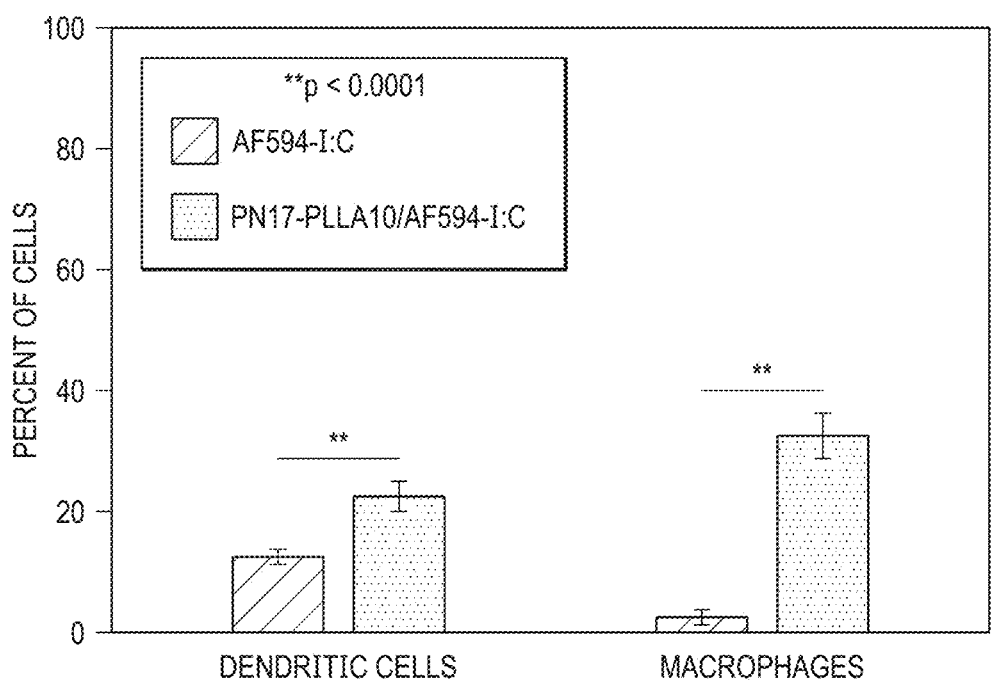
Figure 7C:
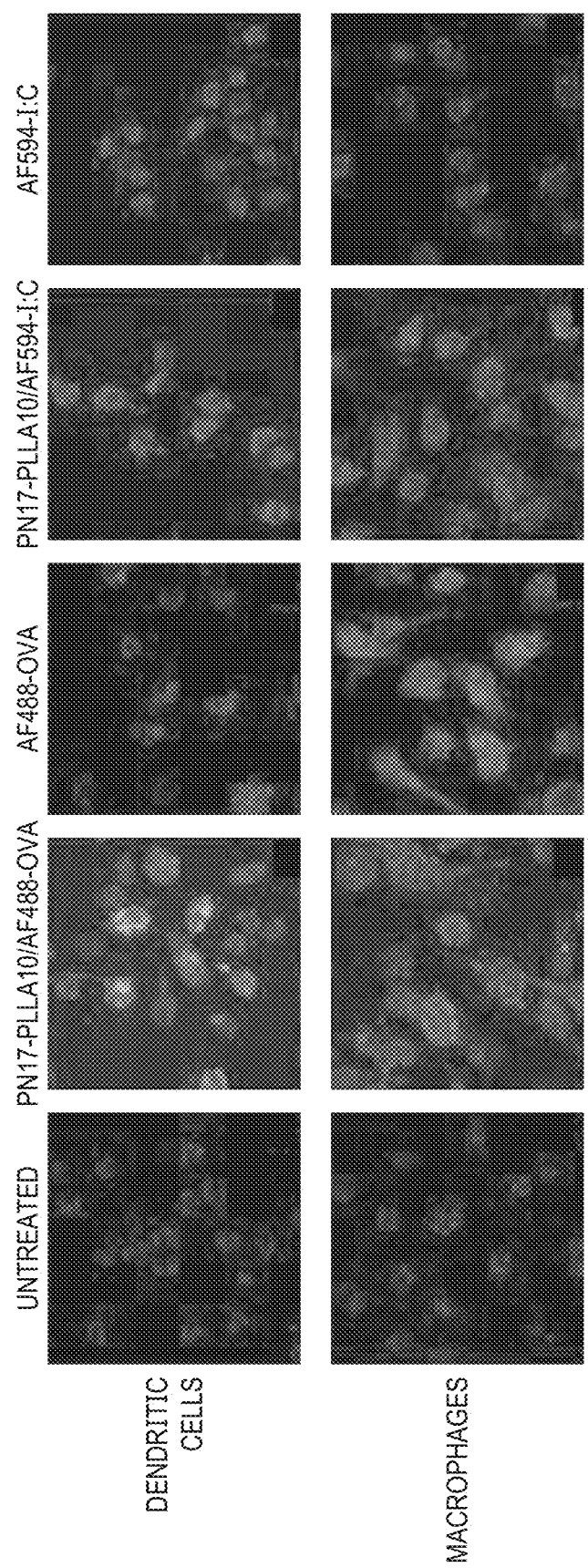

FIGS. 7A-7C illustrate cellular uptake in accordance with an illustrative embodiment. FIGS. 7A-7C illustrate cellular uptake of (A) PN17-PLLA10/AF488-OVA, free OVA, (B) PN17-PLLA10/AF594-Poly(1:C) and free AF594-Poly(I:C) in BMDC and BMDM after three hours incubation at 37° C. FIG. 7C illustrates confocal images of cellular localization with the various formulations. AF488-OVA is shown in green, and AF594-I:C is shown in red. Scale bar represents 10 µm.

The cellular uptake of PN17-PLLA10/AF488-OVA and PN17-PLLA10/AF594-I:C is studied using bone marrow derived dendritic cells (BMDC) and macrophages (BMDM). In BMDC, the uptake of the OVA complexed with PN17-PLLA10 is significantly higher compared to free OVA. However, there is no significant difference between PN17-PLLA10/AF488-OVA and free OVA in BMDM, as shown in FIG. 7A. As for AF594-1:C, the cellular uptake is significantly higher for both BMDC and BMDM when Poly(I:C) is complexed with PN17-PLLA10 as compared to free Poly(I:C). The same phenomenon is also evident in confocal microscopy images shown in FIG. 7C, where more AF488-OVA and AF594-I:C entered into dendritic cells when delivered with PN17-PLLA10. With higher cellular uptake of OVA and Poly(I:C) when delivered using the cationic polymer PN17-PLLA10 in the major antigen presenting cells—dendritic cells, higher stimulation and induction of immune response can occur.

Vaccination and Production of Anti-OVA IgG1

Figure 8C:
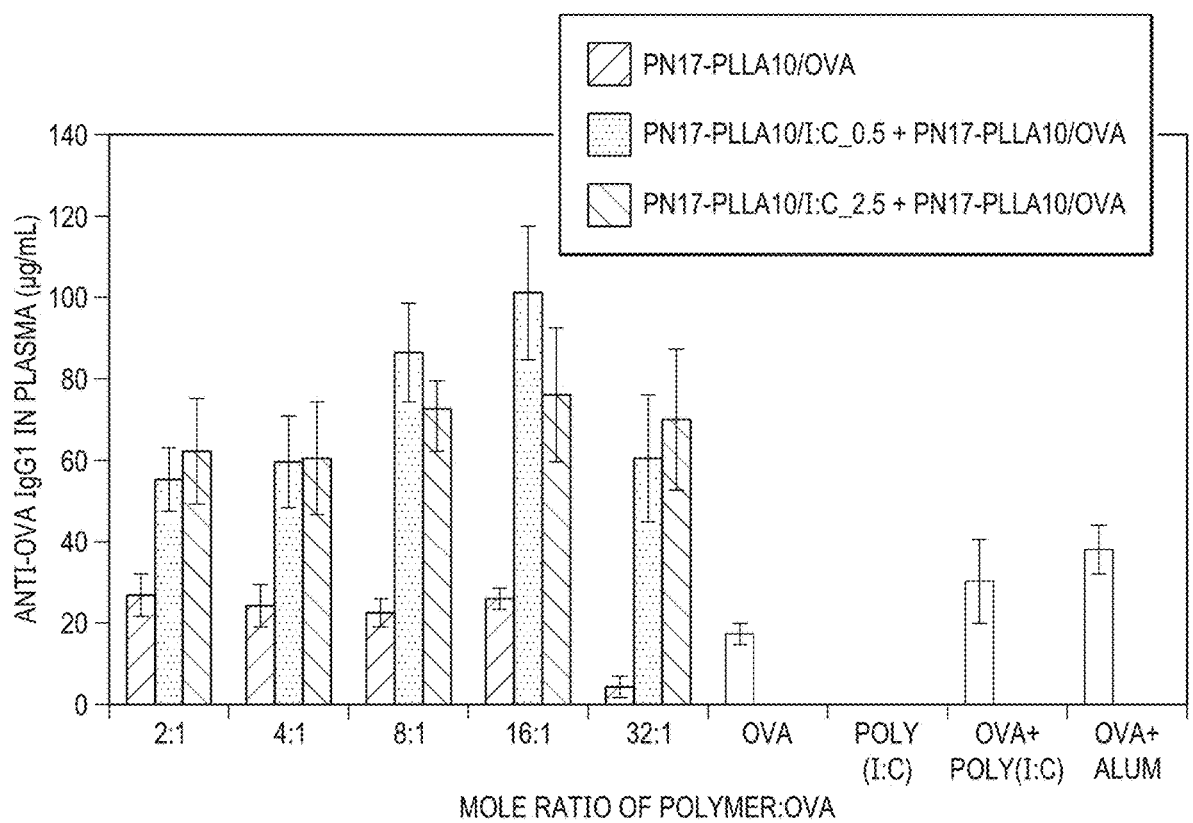

FIGS. 8A-8C illustrate amount of anti-OVA IgG1 present in mouse blood plasma at one-month post-vaccination in accordance with an illustrative embodiment. Vaccination of mice can evoke immune response against OVA, resulting in the production of anti-OVA antibodies. In particular, OVA-specific IgG1 antibody subclass account for a large proportion of the antibodies produced. In accordance with the illustrative embodiments, the plasma levels of anti-OVA IgG1 antibodies at two different time points (one month and nine months post-vaccination) are analyzed via ELISA. In the first experiment, mice are vaccinated with PN30-PLLA25/OVA and PN17-PLLA10/OVA nanoparticles and analyzed for the amount of anti-OVA IgG1 present in blood plasma at one month post-vaccination. Mice that are vaccinated with PN17-PLLA10/OVA nanoparticles generally produced higher quantity of anti-OVA IgG1 compared to those injected with PN30-PLLA25/OVA NP. At polymer to OVA molar ratio 2:1 to 16:1, mice that were vaccinated with PN17-PLLA10/OVA NP produced higher amount of anti-OVA IgG1 antibodies as compared to using OVA alone ($p<0.05$). However, with the more cationic PN30-PLLA25/OVA NP, the amount of anti-OVA IgG1 antibodies produced is similar to those vaccinated with OVA alone. This indicates the strong influence that the molecular weight and charge content have on the vaccination efficacy, as shown in FIG. 8A.

Clearly, the use of PN17-PLLA10 at polymer to OVA ratios of 2:1 to 16:1 increased the amount of the antibodies being produced as compared to OVA alone one-month post-administration, as shown in FIG. 8B, and the amount of the antibodies produced by the use of PN17-PLLA10/OVA particles is comparable with that produced by the use of OVA/Alum particles. These results demonstrate potential of the polymer for use as an alternative adjuvant. As an attempt to further boost the immunostimulation effects of OVA, an adjuvant poly(I:C) is incorporated during the loading of OVA into the nano- and micro-particles.

Interestingly, when poly(I:C) is delivered together with OVA in the same particle, there is a significantly higher amount of anti-OVA IgG1 antibodies produced as compared to those stimulated with PN17-PLLA10/OVA particles alone at polymer to OVA molar ratio 4:1 to 32:1, as shown in FIG. 8B. This correlates with the amount of polymer used for complexation and is independent of the size of the particles, thereby suggesting the importance of the cationic polymer in stimulating the immune response towards OVA. Moreover, vaccination with PN17-PLLA10/OVA/I:C particles at polymer to OVA molar ration 4:1 to 16:1 also result in the production of more anti-OVA IgG1 antibodies as compared to vaccination with Poly(I:C) or Alum ($p<0.05$), as shown in FIG. 8B. Importantly, the subjects did not display any symptoms associated with toxicity such as lethargy, muscle loss, dehydration, or anorexia throughout the one-month study period, hence suggesting good in vivo tolerance.

When Poly(I:C) and OVA are loaded separately into the polymeric nanoparticles and given to the mice with injections scheduled 5 mins apart at the same site, the amount of anti-OVA IgG1 antibodies produced is also higher compared to PN17-PLLA10/OVA particles, OVA+Poly(I:C) and OVA+Alum ($P<0.05$), as shown in FIG. 8C. In this case, the amount of anti-OVA IgG1 antibodies is similar between groups that were vaccinated with PN17-PLLA10/I:C_0.5+PN17/PLLA10/OVA and PN17-PLLA10/I:C_2.5+PN17/PLLA10/OVA, indicating that the amount of cationic polymer present in the Poly(I:C)-loaded particles did not influence the immune response.

In the next experiment, the long-term immunity provided by the various formulations is investigated by analyzing the amount of anti-OVA IgG1 antibodies present in mouse blood at nine months post-vaccination. FIG. 9 illustrates an amount of anti-OVA IgG1 present in mouse blood plasma at nine-month post-vaccination in accordance with an illustrative embodiment. As seen in FIG. 9, immunization carried out using formulations containing polymeric nanoparticles are significantly more effective with a higher amount of anti-OVA IgG1 antibodies produced as compared to using just OVA alone ($P<0.05$). Interestingly, it is apparent that the cationic polymer play an important role in increasing the vaccination efficacy as all formulations that contain both the polymer and adjuvant Poly(I:C) (FIG. 9, Groups 1 to 3) result in significantly higher amount of anti-OVA IgG1 antibodies as compared to OVA+Poly(I:C) (FIG. 9, Group 5) ($P<0.05$) regardless of whether the adjuvant Poly(I:C) is delivered together in the same nanoparticle as OVA (FIG. 9, Group 1) or separately (FIG. 9, Groups 2 and 3). In addition, vaccination efficacy for formulations that contain the cationic polymers is independent on the presence of Poly(I:C) (P>0.05) (FIG. 9, Groups 1 to 3 vs. Group 4). Similar to one-month post-administration, the use of the polymer increased vaccination efficacy at nine-month post-administration (FIG. 9, Group 4 vs. Group 6).

Long-Term Immunity Against Tumors

A study on the long-term anticancer immunity is carried out by challenging mice vaccinated nine months earlier with EG.7-OVA tumor cells. The mice are considered middle-aged in their lifespan as they are 13 months old at the time of cancer challenge. FIG. 10 shows changes in tumor size as a function of time in accordance with an illustrative embodiment. EG.7-OVA cells are inoculated into the subcutaneous region of C57/BL6 mice at nine months post-vaccination. Immunization carried out using PN17-PLLA10/OVA is more effective compared to Poly(I:C)+OVA and OVA alone as there is significant difference in tumor size between Day 12 to Day 27 post-administration of tumor cells, as seen in FIG. 10. Comparing the effectiveness in tumor rejection between the various formulations, those that contain both the cationic polymer and adjuvant Poly(I:C) are superior compared to OVA+Poly(I:C) and OVA alone (P<0.05). Interestingly, when Poly(I:C) and OVA are delivered using separate particles as in formulations PN17-PLLA10/I:C_0.5+PN17-PLLA10/OVA and PN17-PLLA10/I:C_2.5+PN17-PLLA10/OVA, the tumors are rejected more effectively as compared to PN17-PLLA10/OVA/I:C where both Poly(I:C) and OVA are given together in the same particle formulation. In particular, the tumor size of mice that are vaccinated with PN17-PLLA10/I:C_0.5+PN17-PLLA10/OVA and PN17-PLLA10/I:C_2.5+PN17-PLLA10/OVA are significantly smaller compared to that of mice vaccinated with OVA+Poly(I:C) and OVA alone (P≤0.05) throughout the study (up to Day 27). Comparatively, mice that are vaccinated with PN17-PLLA10/OVA/I:C have smaller tumors (P≤0.05) only up to Day 19 post-administration of tumor cells.

Effects on Innate and Adaptive Immune Response

Figure 11B:
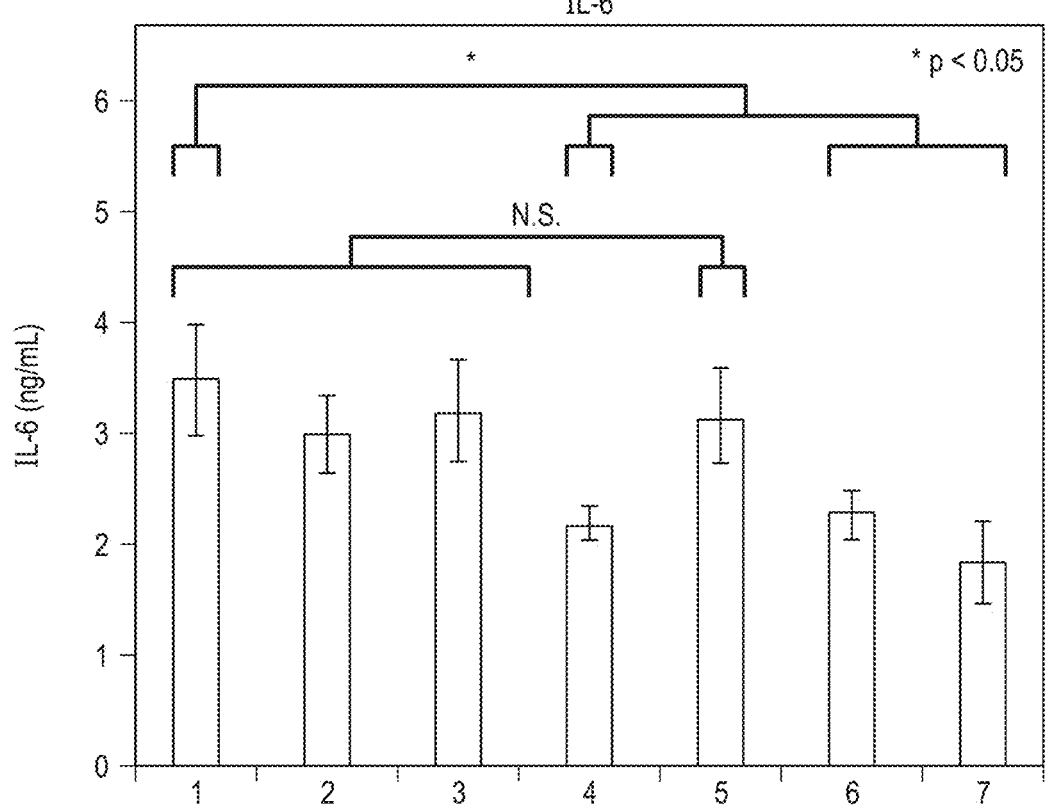
Figure 11D:
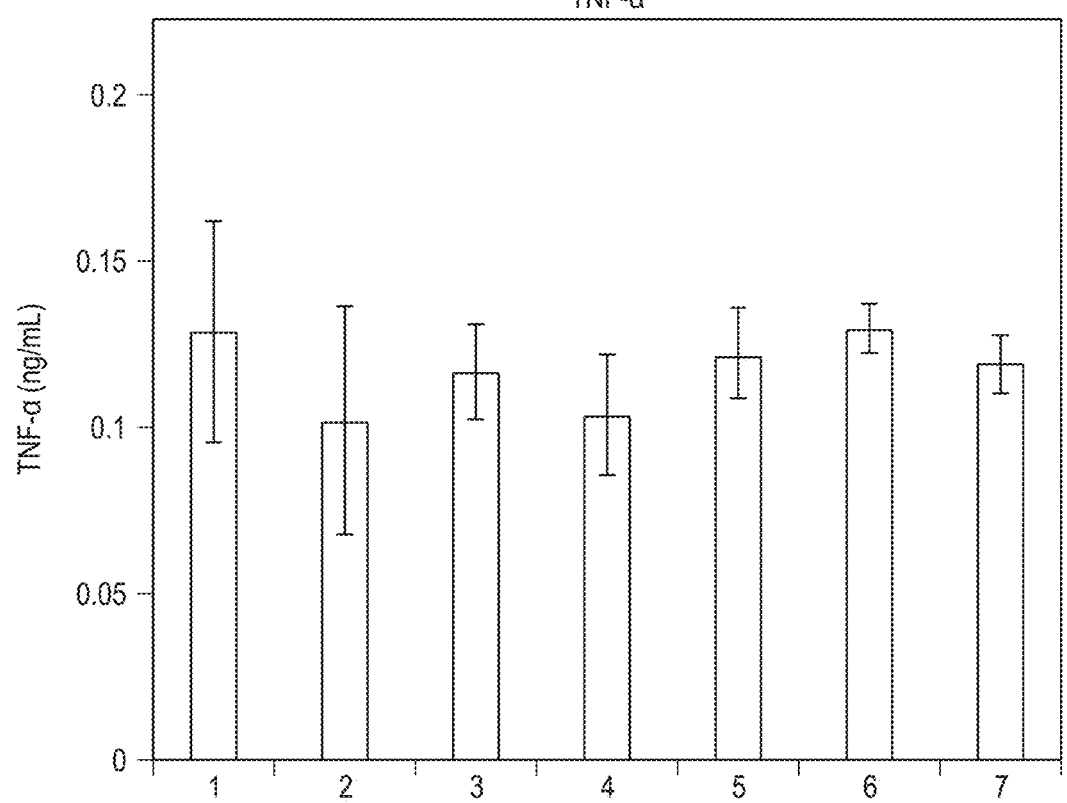

Cytokine production can change in response to vaccination. The effects of adjuvants of the illustrative embodiments on the cytokine levels of two cytokines commonly associated with both innate and adaptive immunity—IL-6 and TNF-α is evaluated. FIGS. 11A-11D show in vivo innate immune response at one month post-vaccination in accordance with an illustrative embodiment. Levels of IL-6 and TNF-α in blood plasma (FIGS. 11A and 11C) and primed splenocyte cultures (FIGS. 11B and 11D), respectively. The Groups in FIGS. 11A-11D are as follows:
 1: PN17-PLLA10/OVA/I:C (16:1)
 2: PN17-PLLA10/I:C_0.5+PN17-PLLA10/OVA (16:1)
 3: PN17-PLLA10/I:C_2.5+PN17-PLLA10/OVA (16:1)
 4: PN17-PLLA10/OVA (16:1)
 5: OVA+Poly(I:C)
 6: OVA
 7: OVA+Alum It has been reported that the production of interleukin-6 (IL-6) is important in the early phase of immunization, to allow for the differentiation of T helper 1 (Th1) cells into CD4+ T cells, which in turn is required for the execution of immune functions. In accordance with the illustrative embodiment, blood plasma samples from mice that were vaccinated with PN17-PLLA10/OVA/I:C (FIG. 11A, Group 1) contained the highest IL-6 levels. Formulations containing Poly(I:C) resulted in significantly higher IL-6 production (FIG. 11A, Groups 2 to 5) compared to those without (FIG. 11A, Groups 6 and 7). Mice that are vaccinated with Alum do not experience any significant changes in IL-6 levels as compared to those vaccinated with only OVA. As for the primed splenocyte cultures from vaccinated mice, those that are vaccinated with PN17-PLLA10/OVA/I:C produce significantly higher amount of IL-6 compared to those vaccinated with PN17-PLLA10/OVA, OVA and OVA+Alum (FIG. 11A, Groups 2, 4, 6 and 7 respectively). There is no significant difference between those vaccinated with PN17-PLLA10/OVA/I:C, PN17-PLLA10/I:C_0.5+PN17-PLLA10/OVA, PN17-PLLA10/I:C_2.5+PN17-PLLA10/OVA and OVA+Poly(I:C) (FIG. 11B, Groups 1, 2, 3 and 5, respectively).

As for TNF-α, there are multiple complicated roles for this cytokine in cancer. In one aspect, TNF-α exerts anti-cancer effects, mainly through inducing cancer cell death. In the other aspect, for cancer cells that are resistant to TNF-induced cytotoxicity, TNF-α stimulates cell proliferation, survival, migration, and angiogenesis, which result in tumor promotion. Thus, TNF-α is a double-edged sword that could be either pro- or anti-tumorigenic. Interestingly, in the illustrative embodiment, there are negligible changes to the levels of TNF-α in both plasma samples (FIG. 11C) and primed splenocytes (FIG. 11D) from vaccinated mice, regardless of the adjuvants present. Thereby, this enables elimination of the contradictive effects of TNF-α level changes.

Cytotoxic T Lymphocyte Induction and Assay

The activation of cytotoxic T lymphocyte activity is crucial in killing cancer cells through T cell-mediated lysis of the malignant cells. When the cytotoxic T cells are activated and brought into contact with target cells, they kill their targets by programming them to undergo apoptosis. The induction of cell death of the antigen-specific target cells can occur within several minutes, although death may take several hours to be completely apparent. FIG. 12 shows cytotoxic T lymphocyte (CTL) responses of various formulation containing OVA in accordance with an illustrative embodiment. The groups in FIG. 12 are as follows:
 1: PN17-PLLA10/OVA/I:C (16:1)
 2: PN17-PLLA10/I:C_0.5+PN17-PLLA10/OVA (16:1)
 3: PN17-PLLA11/I:C_2.5+PN17-PLLA10/OVA (16:1)
 4: PN17-PLLA10/OVA (16:1)
 5: OVA+Poly(I:C)
 6: OVA
 7: OVA+Alum To study this effect, the mice are immunized with various OVA formulations and compared against OVA without adjuvants (Control: FIG. 12, Group 6). Interestingly, the splenocytes isolated from mice that are vaccinated with PN17-PLLA10/I:C_0.5+PN17-PLLA10/OVA and PN17-PLLA10/I:C_2.5+PN17-PLLA10/OVA show the highest average relative cytotoxic T lymphocyte (CTL) responses against EG.7-OVA cells compared to all other formulations. It is also important to note that the CTL activity of groups that are vaccinated with formulations containing polymer adjuvants are similar (no significant difference) compared to the one containing aluminum-based adjuvant as the positive control (FIG. 12, Group 7). The results from this study indicate that the polymer adjuvants can perform as well as widely-used clinical adjuvant, Alum, in inducing cytotoxic T lymphocytes for cancer cell elimination.

Figures 13A, 13B:
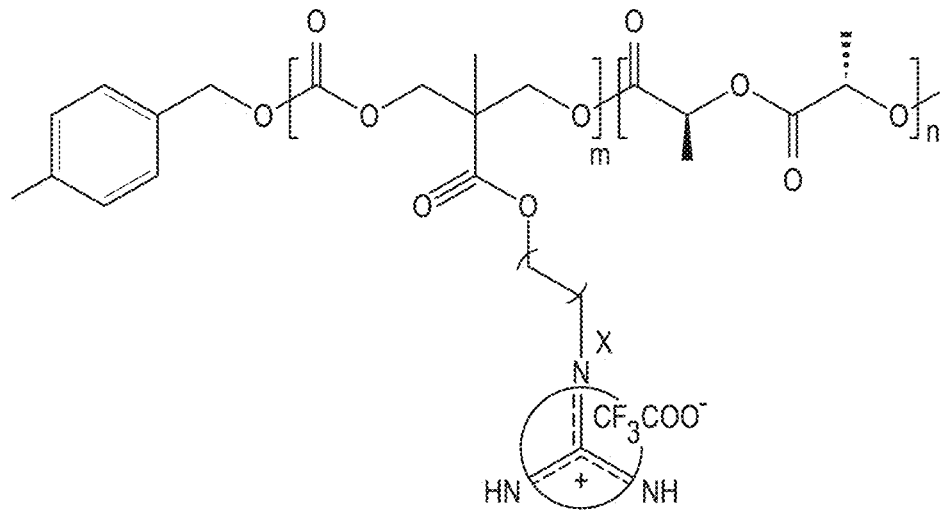
FIGS. 13A and 13B illustrate the chemical structure of guanidinium-based adjuvants in accordance with an illustrative embodiment.

Different Polymer Adjuvant Candidates Created Through Facile Synthetic Strategies In accordance with an alternative embodiment, Poly (Ethyl-Guanidinium) and Poly(Butyl-Guanidinium) are used as potential adjuvants. FIGS. 13A and 13B illustrate the chemical structure of guanidinium-based adjuvants in accordance with an illustrative embodiment. A total of two vaccination shots are given at day 0 and 4 weeks.

Figure 15A:
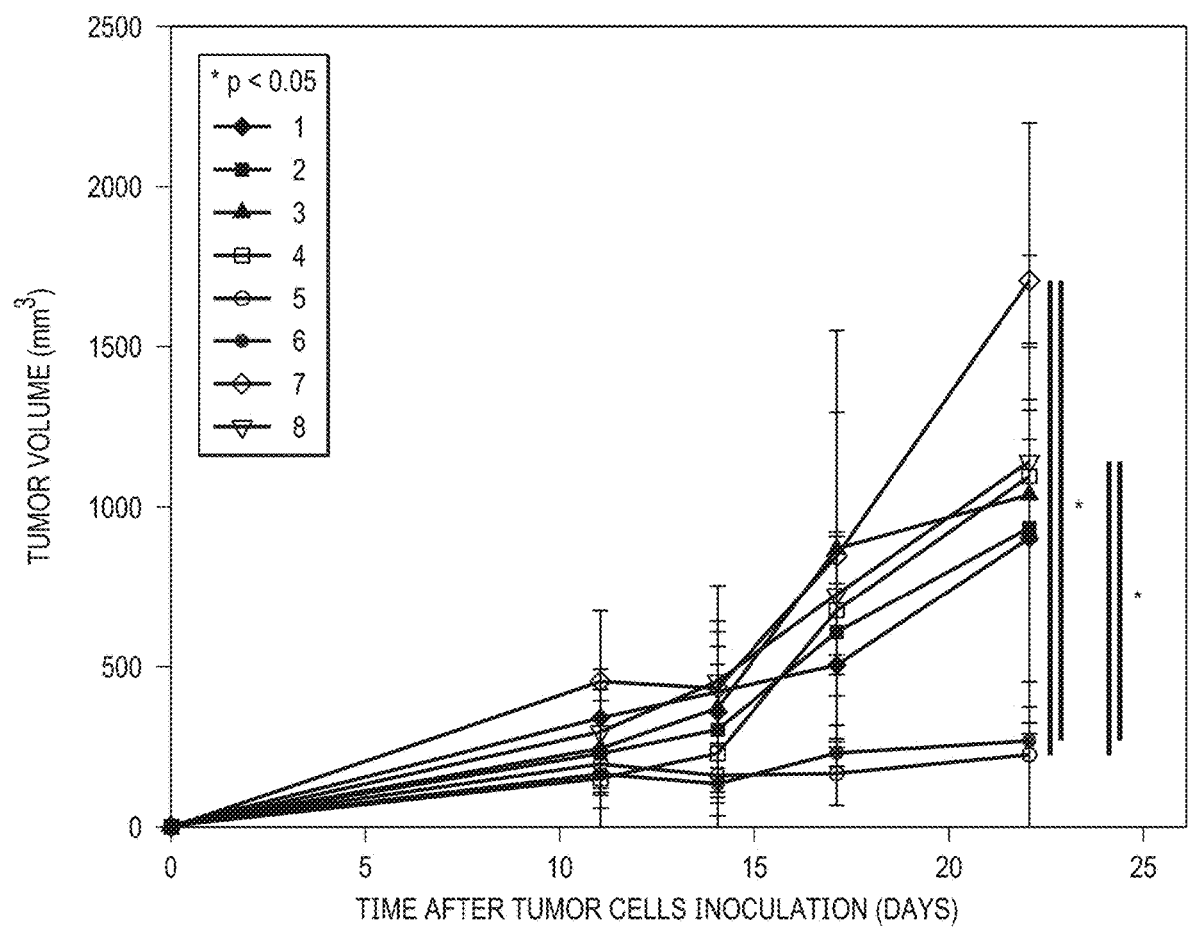
FIGS. 15A and 15B show changes in tumor size as a function of time for guanidinium-based adjuvants in accordance with an illustrative embodiment.
Figure 15B:
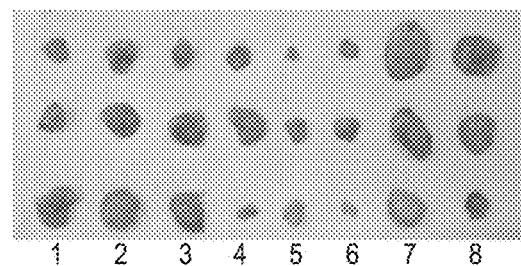

Blood samples are taken at four weeks and seven weeks post-vaccination. FIGS. 14A and 14B show vaccination and production of anti-OVA IgG1 in accordance with an illustrative embodiment. The Groups in FIGS. 14A and 14B are as follows:
1: PEt_Gua20/OVA (1:1)
2: PEt_Gua20/OVA (1:1)+PEt_Gua20/IC_2.5
3: PEt_Gua20/OVA (1.9:1)
4: PEt_Gua20/OVA (1.9:1)+PEt_Gua20/IC_2.5
5: PBut_Gua20/OVA (1:1)
6: PBut_Gua20/OVA (1:1)+PBut_Gua20/IC_2.5
7: OVA
8: OVA+Alum At four weeks, formulations in Group 2, 3, 4 and 6 result in significantly higher amounts of anti-OVA IgG antibodies being produced compared to OVA+Alum and OVA control group. A booster shot is given at four weeks after the first vaccination. The formulation in Group 4 results in a significantly higher amount of anti-OVA IgG antibodies being produced compared to the OVA+Alum and OVA control group. FIGS. 15 and 15B show changes in tumor size as a function of time for guanidinium-based adjuvants in accordance with an illustrative embodiment. The Groups for FIG. 15B are as follows:
1: PEt_Gua20/OVA (1:1)
2: PEt_Gua20/OVA (1:1)+PEt_Gua20/IC_2.5
3: PEt_Gua20/OVA (1.9:1)
4: PEt_Gua20/OVA (1.9:1)+PEt_Gua20/IC_2.5
5: PBut_Gua20/OVA (1:1)
6: PBut_Gua20/OVA (1:1)+PBut_Gua20/IC_2.5
7: OVA
8: OVA+Alum Formulations in Groups 5 and 6 result in significantly reduced tumor progress compared to OVA+Alum and OVA control group.

Figure 16:
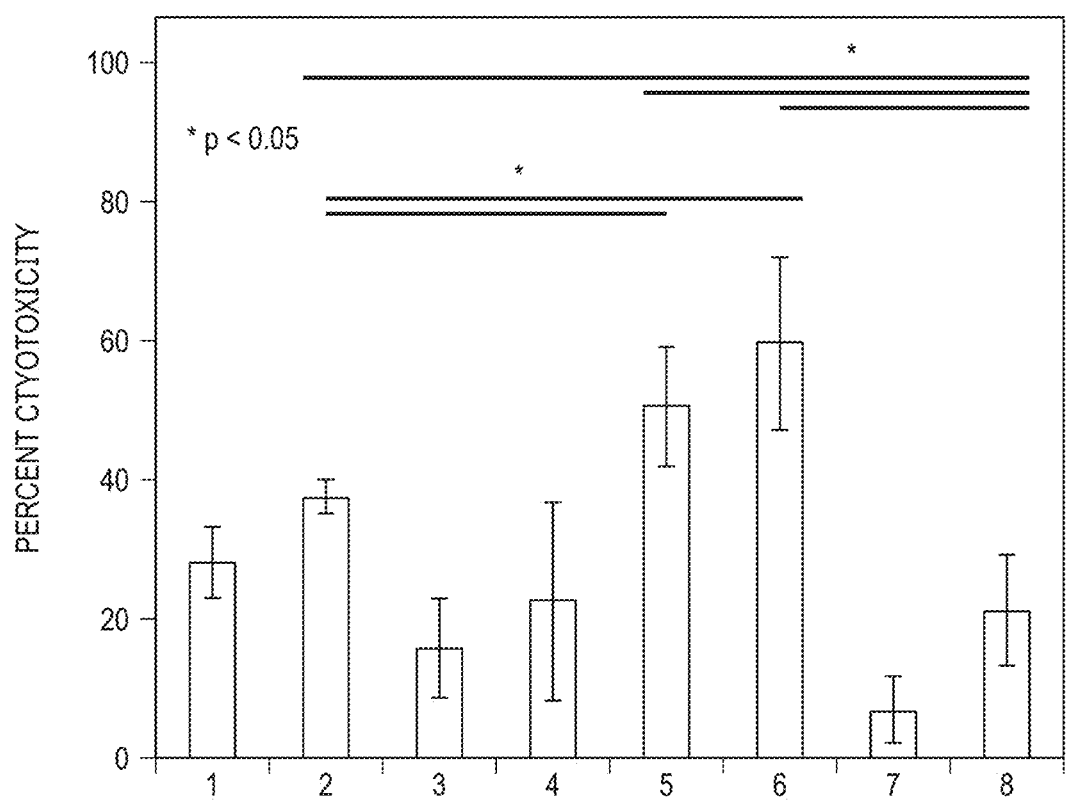
FIG. 16 shows cytotoxic T lymphocyte (CTL) activity at seven weeks post-vaccination in accordance with an illustrative embodiment.

FIG. 16 shows cytotoxic T lymphocyte (CTL) activity at seven weeks post-vaccination in accordance with an illustrative embodiment. The Groups for FIG. 16 are as follows:
1: PEt_Gua20/OVA (1:1)
2: PEt_Gua20/OVA (1:1)+PEt_Gua20/IC_2.5
3: PEt_Gua20/OVA (1.9:1)
4: PEt_Gua20/OVA (1.9:1)+PEt_Gua20/IC_2.5
5: PBut_Gua20/OVA (1:1)
6: PBut_Gua20/OVA (1:1)+PBut_Gua20/IC_2.5
7: OVA
8: OVA+Alum Cytotoxic T cells are retrieved from the spleens of vaccinated mice and co-cultured with EG7.OVA tumor cells to check for cytotoxic activity. Significantly higher cytotoxic T cell activity are seen from cells treated with Group 5 and 6 formulation. This is probably the cause for reduced tumor progression in mice.

Figure 17:
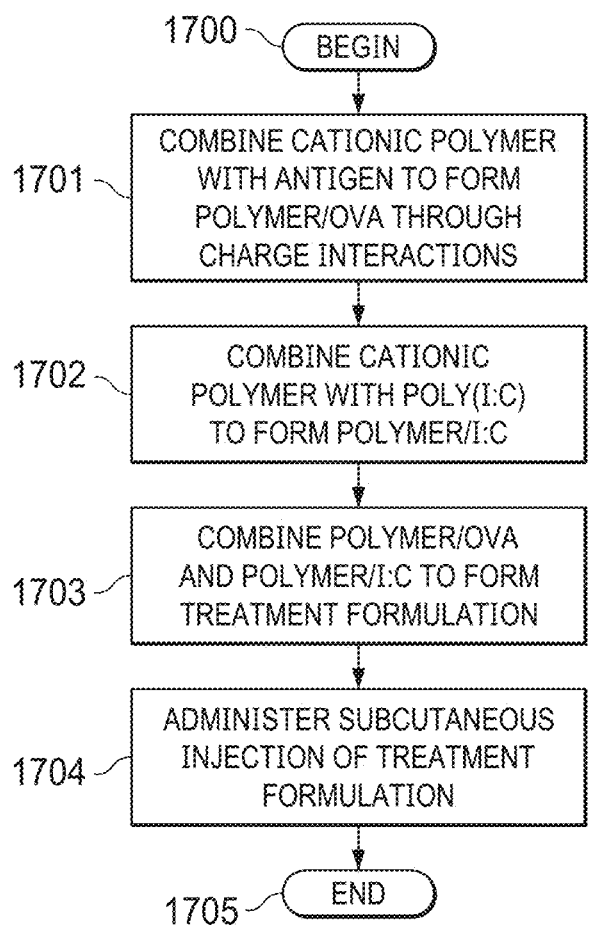
FIG. 17 is a flowchart illustrating formation of a vaccine in accordance with an illustrated embodiment.

FIG. 17 is a flowchart illustrating formation of a vaccine in accordance with an illustrated embodiment. Operation begins (block 1700), and a cationic polymer is combined with an antigen, such as ovalbumin, through charge interactions to form polymer/OVA nano- or micro-particles (block 1701). The cationic polymer is also combined with a polyinosinic: polycytidylic acid (poly(I:C)) to form polymer/I:C nano- or micro-particles (block 1702). The polymer/OVA particles and polymer/I:C particles are combined to form a treatment formulation (block 1703). Then, the treatment formulation is administered by subcutaneous injection (block 1704). Thereafter, operation ends (block 1705).

The illustrative embodiments described herein successfully demonstrate the use of nano- and micro-sized particles containing both cationic polymers and Poly(I:C) as adjuvants for vaccine. The complexation between the polymer and poly(I:C) formed compact nanoparticles. Although the complexation between cationic polymer and OVA show wide variation with regards to size and zeta potential of the complexes, this does not have apparent effect on the vaccination efficacy of the formulations. From bioimaging results, the amount of OVA-loaded nanocomplexes present at the site of injection is higher compared to the OVA alone at all the time points and it is therefore highly possible that immunostimulation occur at nearby non-lymphoid tissue. The molecular weight and charge content have a strong impact on the vaccination efficacy as mice that are vaccinated with PN17-PLLA10/OVA particles produce a higher amount of anti-OVA IgG1 antibodies as compared to the more cationic PN30-PLLA25/OVA particles. PLLA10/OVA lead to a comparable amount of anti-OVA IgG1 antibodies produced in plasma as compared to Alum. When an additional adjuvant poly(I:C) is incorporated into the formulations containing the cationic polymer PN17-PLLA10, there is significant improvement in the vaccination efficacy with a higher amount of anti-OVA IgG1 antibodies produced and greater resilience against OVA-expressing tumor cells. More importantly, the cationic polymers are not associated with any adverse in vivo effects. Therefore, the cationic polymers have great potential use as vaccine adjuvants.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for formation of a vaccine comprising:
combining a cationic polymer adjuvant with an antigen to form first immunoparticles through charge interactions;
producing a treatment formulation for the vaccine comprising the first immunoparticles, and
combining the cationic polymer adjuvant to a polyinosinic:polycytidylic acid (poly(I:C)) to form second immunoparticles and producing the treatment formulation comprising the first immunoparticles and the second immunoparticles.

2. The method of claim 1, wherein the cationic polymer adjuvant is a biodegradable polymer.

3. The method of claim 1, wherein the antigen comprises ovalbumin.

4. The method of claim 1, wherein the cationic polymer adjuvant comprises PN17-PLLA10 poly-L-lactide nanoparticles.

5. The method of claim 1, wherein the first immunoparticles have an adjuvant/antigen mole ratio of 16:1.

6. A method for administering a treatment formulation, comprising:

combining a cationic polymer adjuvant with an antigen to form first immunoparticles through charge interactions;

producing a treatment formulation for the vaccine comprising the first immunoparticles;

combining the cationic polymer adjuvant to a polyinosinic:polycytidylic acid (poly(I:C)) to form second immunoparticles and producing the treatment formulation comprising the first immunoparticles and the second immunoparticles; and administering the treatment formulation by subcutaneous injection.

7. The vaccine of claim 6, wherein the cationic polymer adjuvant is a biodegradable polymer.

8. The vaccine of claim 6, wherein the antigen comprises ovalbumin.

9. The vaccine of claim 6, wherein the cationic polymer adjuvant comprises PN17-PLLA10 poly-L-lactide nanoparticles.

10. The vaccine of claim 6, wherein the first immunoparticles have an adjuvant/antigen mole ratio of 16:1.

11. A vaccine comprising:

first immunoparticles formed by combining a cationic polymer adjuvant with an antigen through charge interactions; and second immunoparticles formed by combining the cationic polymer adjuvant with polyinosinic:polycytidylic acid (poly(I:C)).

12. The vaccine of claim 11, wherein the cationic polymer adjuvant is a biodegradable polymer.

13. The vaccine of claim 11, wherein the antigen comprises ovalbumin.

14. The vaccine of claim 11, wherein the cationic polymer adjuvant comprises PN17-PLLA10 poly-L-lactide nanoparticles.

15. The vaccine of claim 11, wherein the immunoparticles have an adjuvant/antigen mole ratio of 16:1.

* * * * *